United States Patent
Mejlhede et al.

(10) Patent No.: US 8,303,549 B2
(45) Date of Patent: *Nov. 6, 2012

(54) INJECTION DEVICE

(75) Inventors: Signe Thorning Mejlhede, Svinninge (DK); Lasse W. Mogensen, Søborg (DK); Steffen Gyrn, Ringsted (DK); Elo Hørdum, Hørsholm (DK)

(73) Assignee: Unomedical A/S, Birkeroed (DK)

( * ) Notice: Subject to any disclaimer, the term of this patent is extended or adjusted under 35 U.S.C. 154(b) by 684 days.

This patent is subject to a terminal disclaimer.

(21) Appl. No.: 12/158,514

(22) PCT Filed: Dec. 22, 2006

(86) PCT No.: PCT/DK2006/000742
§ 371 (c)(1),
(2), (4) Date: Dec. 9, 2008

(87) PCT Pub. No.: WO2007/071258
PCT Pub. Date: Jun. 28, 2007

(65) Prior Publication Data
US 2009/0221971 A1 Sep. 3, 2009

Related U.S. Application Data

(60) Provisional application No. 60/753,684, filed on Dec. 23, 2005, provisional application No. 60/762,374, filed on Jan. 25, 2006, provisional application No. 60/816,767, filed on Jun. 27, 2006.

(30) Foreign Application Priority Data

Jan. 24, 2006 (DK) .................................. 2006 00104

(51) Int. Cl.
*A61M 5/00* (2006.01)

(52) U.S. Cl. ........ 604/244; 604/180; 604/200; 604/201; 604/205; 604/236

(58) Field of Classification Search ................. 604/174, 604/175, 180, 181, 200, 201, 236, 244, 256, 604/131, 138, 139, 148, 93.01, 288.02, 205
See application file for complete search history.

(56) References Cited

U.S. PATENT DOCUMENTS
1,592,462 A 7/1926 MacGregor
(Continued)

FOREIGN PATENT DOCUMENTS
DE 4 342 329 A1 6/1994
(Continued)

OTHER PUBLICATIONS

"Why inset®?" inset® infusion set product overview; http://web.archive.org/web/20040906102448/http://www.infusion-set.com/Default.asp?ID=108; two pages, 2004.

(Continued)

*Primary Examiner* — Bhisma Mehta
(74) *Attorney, Agent, or Firm* — Brinks Hofer Gilson & Lione

(57) ABSTRACT

The application relates to a device for an intermittent or continuous administration of a therapeutical substance, such as insulin, including a base part to which an injection part and a delivery part are fastened. The delivery part includes a reservoir and a pump, and the injection part includes base plate, a cannula part with a body with a through-going opening, and at least one cannula having a proximal end protruding from the lower side of the body and an adhesive portion for fastening the base plate to the skin of the user. The delivery part and the injection part are assembled through a connector having a fluid path leading fluid from the reservoir to the through-going opening in the cannula part.

12 Claims, 22 Drawing Sheets

U.S. PATENT DOCUMENTS

| | | |
|---|---|---|
| 2,047,010 A | 7/1936 | Dickinson |
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A * | 5/1977 | Tenczar ................ 604/411 |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olsen |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teisson-Simony |
| 5,527,287 A | 6/1996 | Miskinyar et al. |
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |

| | | | | | | |
|---|---|---|---|---|---|---|
| 5,558,650 | A | 9/1996 | McPhee | 6,077,244 | A | 6/2000 | Botich et al. |
| 5,562,629 | A | 10/1996 | Haughton et al. | 6,079,432 | A | 6/2000 | Paradis |
| 5,562,636 | A | 10/1996 | Utterberg | 6,086,008 | A | 7/2000 | Gray et al. |
| 5,573,510 | A | 11/1996 | Isaacson | 6,086,575 | A | 7/2000 | Mejslov |
| 5,575,777 | A | 11/1996 | Cover et al. | 6,090,068 | A | 7/2000 | Chanut |
| 5,584,813 | A | 12/1996 | Livingston et al. | 6,093,172 | A | 7/2000 | Funderburk et al. |
| 5,586,553 | A | 12/1996 | Halili | 6,093,179 | A | 7/2000 | O'Hara et al. |
| 5,591,188 | A | 1/1997 | Waisman | 6,099,503 | A | 8/2000 | Stardella |
| 5,599,309 | A | 2/1997 | Marshall et al. | 6,105,218 | A | 8/2000 | Reekie |
| 5,599,315 | A | 2/1997 | McPhee | 6,106,498 | A | 8/2000 | Friedli et al. |
| 5,599,318 | A | 2/1997 | Sweeney et al. | 6,120,482 | A | 9/2000 | Szabo |
| 5,628,765 | A | 5/1997 | Morita | 6,123,690 | A | 9/2000 | Mejslov |
| 5,643,214 | A | 7/1997 | Marshall | 6,132,755 | A | 10/2000 | Eicher et al. |
| 5,643,216 | A | 7/1997 | White | 6,139,534 | A | 10/2000 | Niedospial, Jr. |
| 5,643,220 | A | 7/1997 | Cosme | 6,159,181 | A | 12/2000 | Crossman et al. |
| 5,662,617 | A | 9/1997 | Odell et al. | 6,183,464 | B1 | 2/2001 | Sharp et al. |
| 5,665,071 | A | 9/1997 | Wyrick | 6,191,338 | B1 | 2/2001 | Haller |
| 5,665,075 | A | 9/1997 | Gyure et al. | 6,193,694 | B1 | 2/2001 | Bell et al. |
| 5,676,156 | A | 10/1997 | Yoon | 6,210,420 | B1 | 4/2001 | Mauze et al. |
| 5,681,323 | A | 10/1997 | Arick | 6,219,574 | B1 | 4/2001 | Cormier et al. |
| 5,695,476 | A | 12/1997 | Harris | 6,221,058 | B1 | 4/2001 | Kao et al. |
| 5,697,907 | A | 12/1997 | Gaba | 6,248,093 | B1 | 6/2001 | Moberg |
| 5,700,250 | A | 12/1997 | Erskine | 6,293,925 | B1 | 9/2001 | Safabash et al. |
| 5,702,371 | A | 12/1997 | Bierman | 6,302,866 | B1 | 10/2001 | Marggi |
| 5,704,920 | A | 1/1998 | Gyure | 6,319,232 | B1 | 11/2001 | Kashmer |
| 5,709,662 | A | 1/1998 | Olive et al. | 6,322,535 | B1 | 11/2001 | Hitchins et al. |
| 5,714,225 | A | 2/1998 | Hansen et al. | 6,322,808 | B1 | 11/2001 | Trautman et al. |
| 5,738,641 | A | 4/1998 | Watson et al. | 6,334,856 | B1 | 1/2002 | Allen et al. |
| 5,741,288 | A | 4/1998 | Rife | 6,355,021 | B1 | 3/2002 | Nielsen et al. |
| 5,752,923 | A | 5/1998 | Terwilliger | 6,364,113 | B1 | 4/2002 | Faasse et al. |
| 5,807,316 | A | 9/1998 | Teeple | 6,379,335 | B1 | 4/2002 | Rigon et al. |
| 5,807,348 | A | 9/1998 | Zinger et al. | 6,387,076 | B1 | 5/2002 | Van Landuyt |
| 5,810,835 | A | 9/1998 | Ryan et al. | 6,387,078 | B1 | 5/2002 | Gillespie, III |
| 5,817,058 | A | 10/1998 | Shaw | 6,405,876 | B1 | 6/2002 | Seshimoto et al. |
| 5,820,598 | A | 10/1998 | Gazza et al. | 6,440,096 | B1 | 8/2002 | Lastovich et al. |
| 5,827,236 | A | 10/1998 | Takahashi | 6,447,482 | B1 | 9/2002 | Rønborg et al. |
| 5,833,666 | A | 11/1998 | Davis et al. | 6,450,992 | B1 | 9/2002 | Cassidy, Jr. |
| 5,843,001 | A | 12/1998 | Goldenberg | 6,485,461 | B1 | 11/2002 | Mason et al. |
| 5,848,990 | A | 12/1998 | Cirelli et al. | 6,488,663 | B1 | 12/2002 | Steg |
| 5,851,197 | A | 12/1998 | Marano et al. | 6,503,222 | B2 | 1/2003 | Lo |
| 5,858,001 | A | 1/1999 | Tsals et al. | 6,517,517 | B1 | 2/2003 | Farrugia et al. |
| 5,865,806 | A | 2/1999 | Howell | 6,520,938 | B1 | 2/2003 | Funderburk et al. |
| 5,899,886 | A | 5/1999 | Cosme | D472,316 | S | 3/2003 | Douglas et al. |
| 5,911,705 | A | 6/1999 | Howell | D472,630 | S | 4/2003 | Douglas et al. |
| 5,913,846 | A | 6/1999 | Szabo | 6,572,586 | B1 | 6/2003 | Wojcik |
| 5,916,199 | A | 6/1999 | Miles | 6,579,267 | B2 | 6/2003 | Lynch et al. |
| 5,919,167 | A | 7/1999 | Mulhauser et al. | 6,582,397 | B2 | 6/2003 | Alesi et al. |
| 5,919,170 | A | 7/1999 | Woessner | 6,595,962 | B1 | 7/2003 | Perthu |
| 5,925,032 | A | 7/1999 | Clements | 6,607,509 | B2 | 8/2003 | Bobroff et al. |
| 5,935,109 | A | 8/1999 | Donnan | 6,607,511 | B2 | 8/2003 | Bobroff et al. |
| 5,947,931 | A | 9/1999 | Bierman | 6,613,064 | B2 | 9/2003 | Rutynowski et al. |
| 5,947,935 | A | 9/1999 | Rhinehart et al. | 6,620,133 | B1 | 9/2003 | Steck |
| 5,951,523 | A | 9/1999 | Osterlind et al. | 6,620,136 | B1 | 9/2003 | Pressly, Sr. et al. |
| 5,954,643 | A | 9/1999 | VanAntwerp et al. | 6,620,140 | B1 | 9/2003 | Metzger |
| 5,957,892 | A | 9/1999 | Thorne | 6,629,949 | B1 | 10/2003 | Douglas |
| 5,957,897 | A | 9/1999 | Jeffrey | 6,645,181 | B1 | 11/2003 | Lavi et al. |
| 5,968,011 | A | 10/1999 | Larsen et al. | 6,645,182 | B1 | 11/2003 | Szabo |
| 5,971,966 | A | 10/1999 | Lav | 6,659,982 | B2 | 12/2003 | Douglas et al. |
| 5,975,120 | A | 11/1999 | Novosel | 6,685,674 | B2 | 2/2004 | Douglas et al. |
| 5,980,488 | A | 11/1999 | Thorne | 6,699,218 | B2 | 3/2004 | Flaherty et al. |
| 5,980,506 | A | 11/1999 | Mathiasen | 6,702,779 | B2 | 3/2004 | Connelly et al. |
| 5,984,224 | A | 11/1999 | Yang | 6,726,649 | B2 | 4/2004 | Swenson et al. |
| 5,984,897 | A | 11/1999 | Peterson et al. | 6,736,797 | B1 | 5/2004 | Larsen et al. |
| D417,733 | S | 12/1999 | Howell et al. | 6,743,203 | B1 | 6/2004 | Pickhard |
| 6,017,328 | A | 1/2000 | Fischell et al. | 6,749,587 | B2 | 6/2004 | Flaherty |
| 6,017,598 | A | 1/2000 | Kreischer et al. | 6,749,589 | B1 | 6/2004 | Douglas et al. |
| D421,119 | S | 2/2000 | Musgrave et al. | 6,755,805 | B1 | 6/2004 | Reid |
| 6,024,727 | A | 2/2000 | Thorne et al. | 6,776,775 | B1 | 8/2004 | Mohammad |
| 6,039,629 | A | 3/2000 | Mitchell | 6,790,199 | B1 | 9/2004 | Gianakos |
| 6,042,570 | A | 3/2000 | Bell et al. | 6,805,686 | B1 | 10/2004 | Fathallah et al. |
| 6,045,533 | A | 4/2000 | Kriesel et al. | 6,808,506 | B2 | 10/2004 | Lastovich et al. |
| 6,045,534 | A | 4/2000 | Jacobsen et al. | 6,811,545 | B2 | 11/2004 | Vaillancourt |
| 6,050,976 | A | 4/2000 | Thorne et al. | 6,814,720 | B2 | 11/2004 | Olsen et al. |
| 6,053,893 | A | 4/2000 | Bucher | 6,824,530 | B2 | 11/2004 | Wagner et al. |
| 6,053,930 | A | 4/2000 | Ruppert | 6,824,531 | B1 | 11/2004 | Zecha, Jr. et al. |
| 6,056,718 | A | 5/2000 | Funderburk et al. | 6,830,562 | B2 | 12/2004 | Mogensen et al. |
| 6,056,726 | A | 5/2000 | Isaacson | 6,837,877 | B2 | 1/2005 | Zurcher |
| 6,074,369 | A | 6/2000 | Sage et al. | 6,837,878 | B2 | 1/2005 | Smutney et al. |
| 6,074,371 | A | 6/2000 | Fischell | 6,840,922 | B2 | 1/2005 | Nielsen et al. |

| | | |
|---|---|---|
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkenson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 * | 12/2007 | Fangrow, Jr. ............. 604/167.02 |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,850,652 B2 | 12/2010 | Liniger et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Pluth et al. |
| 2002/0072720 A1 | 6/2002 | Hague et al. |
| 2002/0074345 A1 | 6/2002 | Scheider et al. |
| 2002/0077599 A1 | 6/2002 | Wojcik |
| 2002/0082543 A1 | 6/2002 | Park et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Davis et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 * | 8/2004 | Hunn et al. ............... 604/164.01 |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |

| | | |
|---|---|---|
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0088271 A1 | 4/2007 | Richards et al. |
| 2007/0093754 A1 | 4/2007 | Mogensen |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheider et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2008/0269687 A1* | 10/2008 | Chong et al. .................. 604/180 |
| 2008/0312601 A1 | 12/2008 | Cane |
| 2009/0062767 A1 | 3/2009 | Van Antwerp et al. |
| 2009/0326456 A1 | 12/2009 | Cross et al. |
| 2010/0004597 A1 | 1/2010 | Gyrn et al. |
| 2010/0137829 A1 | 6/2010 | Nielsen et al. |
| 2010/0228226 A1 | 9/2010 | Nielsen |
| 2010/0262078 A1 | 10/2010 | Blomquist |

FOREIGN PATENT DOCUMENTS

| | | |
|---|---|---|
| DE | 196 31 921 A1 | 3/1997 |
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 A1 | 12/1995 |
| EP | 0714631 B1 | 6/1996 |
| EP | 0744183 A2 | 11/1996 |
| EP | 0747006 A1 | 12/1996 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 0775501 B1 | 6/2002 |
| EP | 1329233 A1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1 527 792 A1 | 5/2005 |
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| JP | 10179734 A | 8/1991 |
| JP | 7051251 A | 11/1995 |
| JP | 8187286 A | 7/1996 |
| JP | A-03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/32981 A1 | 7/1996 |
| WO | WO 96/20021 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |

| | | | |
|---|---|---|---|
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/040083 A2 | 5/2002 |
| WO | WO 02/053220 A2 | 7/2002 |
| WO | WO 02/081012 A2 | 10/2002 |
| WO | WO 02/081013 A2 | 10/2002 |
| WO | WO 02/083206 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 02/068014 A3 | 1/2003 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2004/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A1 | 8/2008 |
| WO | WO 2008/092959 A1 | 8/2008 |
| WO | WO 2008/135098 A1 | 11/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |
| WO | WO 2010/003885 A1 | 1/2010 |
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/112521 A1 | 10/2010 |
| WO | WO 2011/012465 A1 | 2/2011 |
| WO | WO 2011/015659 A1 | 2/2011 |

OTHER PUBLICATIONS

International-Type Search Report for Danish Application No. DK 2006/00104 completed Sep. 20, 2006, 4 pages.
International Search Report for International Application No. PCT/DK2006/000742 completed Feb. 21, 2007, 3 pages.

* cited by examiner

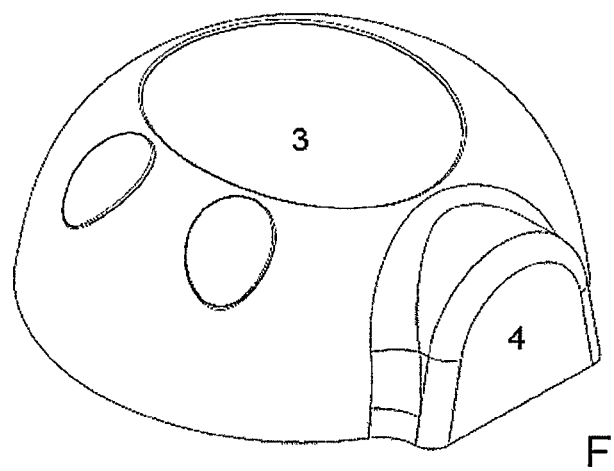
Fig. 20
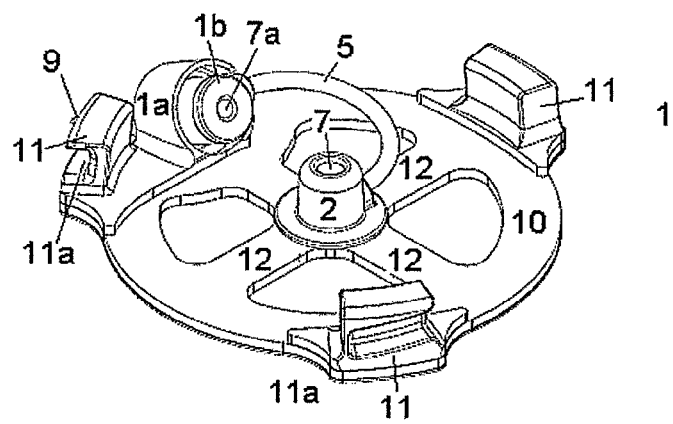
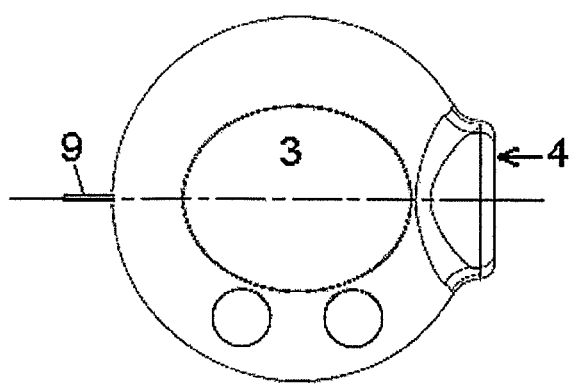
Fig. 21
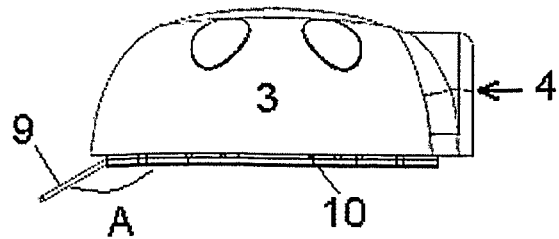

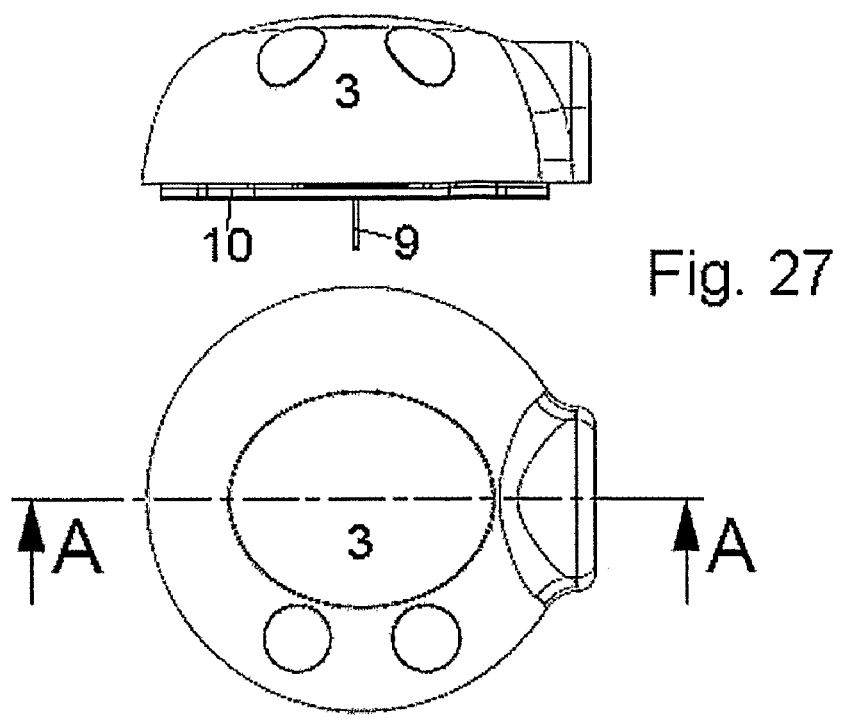
Fig. 27
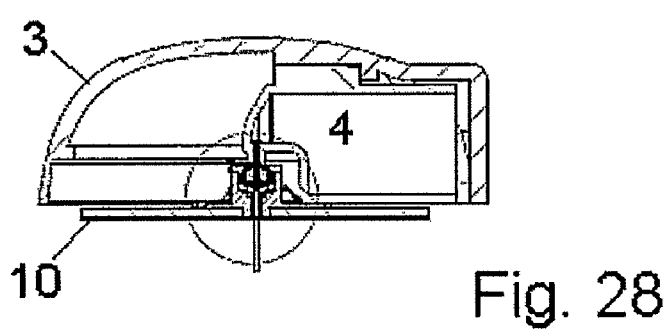
Fig. 28
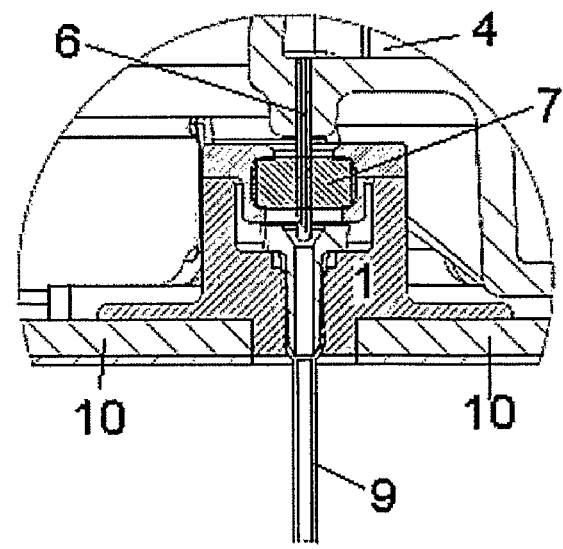

INJECTION DEVICE

This application claims the benefit under 35 U.S.C. §371 of International Application No. PCT/DK2006/000742, filed Dec. 22, 2006, which claims the benefit of U.S. Provisional Application Ser. No. 60/753,684, filed Dec. 23, 2005, Danish Patent Application No. PA 2006 00104, filed Jan. 24, 2006, and U.S. Provisional Application Ser. Nos. 60/762,374, filed Jan. 25, 2006 and 60/816,767, filed Jun. 27, 2006. These references are incorporated herein in their entirety.

THE TECHNICAL FIELD

The invention relates to a device for an intermittent or continuous administration of a therapeutical substance, such as insulin, comprising a base part to which an injection part and a delivery part are fastened. The delivery part comprises a reservoir and a pump, and the injection part comprises a body with a through-going opening, and at least one cannula having a proximal end protruding from the lower side of the body.

PRIOR ART

EP-A1-1.527.792 describes a medical device comprising a transdermal access unit and a reservoir. The transdermal access unit comprises transdermal access means for transporting a fluid through a skin portion of a subject, and a mounting surface adapted for application to the skin of the subject. The reservoir unit comprises a reservoir adapted to contain a fluid drug and an outlet allowing the transdermal access means to be arranged in fluid communication with an interior of the reservoir. Also the device comprise means for expelling e.g. a pump which means during use expels a fluid drug out of the reservoir and through the skin of the subject via the transdermal access means. The transdermal access unit and the reservoir unit further comprise releasable mating coupling means allowing the reservoir unit to be secured to the transdermal access unit during use. The object of the invention is to provide a skin mountable drug delivery device or system which allows such a device or system to be used in a convenient and cost-effective manner.

According to this document the insertion needle of the described embodiments is pivotably arranged inside the needle housing and can be moved between an extended and an extracted position. When the injection needle is inserted it penetrates a membrane in order to penetrate the skin of the subject. According to the present invention a subcutaneously placed cannula is stationary in relation to the base part of the device where the base part is somehow adhered to the user.

US 2004/0204673 A1 describes a lightweight and low cost fluid delivery device capable of adjustable and programmable fluid delivery includes a housing that surrounds a reservoir chamber. In fluid communication with the reservoir chamber is a dispenser for dispensing the fluid from the reservoir in finite amounts. The dispenser is controlled by an electronic microcontroller of the fluid delivery device. The fluid delivery device further includes a communication element that receives information from a remote control device not mechanically attached to the fluid delivery device of the present invention. Also included is an exit port assembly in fluid communication with the dispenser from which the liquid medication exits the fluid delivery device and enters the body of a mammalian patient transcutaneously.

The housings shown in US 2004/0204673 can each be made from flexible material, or can be provided with flexible hinged sections that allow the fluid delivery device to flex during patient movement to prevent detachment and aid in patient comfort but there are no directions as to how such a hinged section should be constructed.

THE INVENTION

The object of the invention is to provide a device for delivering fluid including a pump, a reservoir and an injection part which device assures a fluid tight connection between the reservoir and the injection part. The devices according to the present invention are constructed with means to provide an easy connection and disconnection of the delivery parts to the injection part and at the same time assure a fluid tight connection and prevent invasion of microorganisms into the parts of the device. According to a preferred embodiment of the invention it is also assured that the wearer will have less discomfort during use of the device as this embodiment has means to reduce the transferal of actions from the relatively heavy delivering part to the injection part when the delivering part is affected by touches or movements.

According to claim 1 the invention comprises a device for delivering fluid comprising an injection part and a fluid delivery which fluid delivery part and injection part can be separated and rejoined part (3, 4), the fluid delivery part comprises a reservoir, transferal means e.g. in form of a pump and a house and the injection part comprises
  a base plate,
  a cannula part comprising a body with a through going opening provided with a cannula extending past the proximal side of the base plate and
  means for fixation of the base plate to the skin of the user
wherein the delivery part and the injection part is assembled through a connector comprising a fluid path leading fluid from the reservoir to the through-going opening in the cannula part which fluid path comprises means for blocking access to the injection part when the connector is disconnected from the delivery part and/or the injection part. According to one embodiment of the invention the device comprises means for blocking the access to the delivery part when the connector is separated from this. This embodiment is normally used when a reservoir of the delivery device can be removed from the injection part and afterwards mounted again for further use. According to this or other embodiment the base plate is provided with fastening means for connecting and disconnecting of the delivery device extending from the distal side of the base plate.

When the connector is a part of the device it is possible to provide a fluid tight connection between the delivery part and the injection part. When constructing the device with and interconnecting part it is also possible to add other advantageous features such as means for reducing impacts transferred from the heavy delivery part to the injection part which is partly inserted into the skin of the user. These features make it more safe and comfortable for the user to wear the device.

A "reservoir" is the part of a device where the liquid is held, the liquid being any kind of medication which has to be delivered to the patient in a certain amount at certain time intervals. The "delivery part" is the part of the device which holds a liquid storage and assures transport of the liquids to the injection part. The "injection part" defines a kind of port which is fastened to the user's skin and provided with means e.g. a cannula for transferring the liquid to the user. The injection part does not comprise any heavy or voluminous parts.

In a preferred embodiment the end openings to the fluid path through the connector are blocked when the connector is disconnected from the delivery part and/or the injection part.

This feature is directed toward products which are intended to be used for a longer time which necessitates that the reservoir can be replaced and e.g. the delivery part can be disconnected. Preferably the openings to the fluid path through the connector are blocked with a membrane which can be penetrated by a needlelike object.

In another preferred embodiment the parts of the device have at least two positions, a first position and a second position, in the first position the outlet from the reservoir is blocked with a first barrier which is not permeable for micro-organisms and the inlet of the through going opening in the injection part is blocked with a second barrier which is not permeable for micro organisms, in the second position an open fluid connection is formed between the reservoir and the through going opening in the injection part by passing the first and the second barrier. One or both of the barriers can comprise a material which can be penetrated by a needlelike object where the opening close on retraction of the needle like object or one or both of the barriers can comprise a hard surface which in one position forms an opening in the area positioned between the outlet of the outlet pipe and the inlet of the through going fluid path and in another position close the through going fluid path. Preferably the injection part and the delivery part are connected to each other by one or more flexible areas. More preferred the connector is connected to one part by one or more non-flexible connection and connected to the other part by a flexible area. Most preferred the connector is connected to the injection part by a flexible area.

In one preferred embodiment the at least one flexible area is constructed of an area with reduced material dimensions.

In another preferred embodiment the at least one flexible area is constructed of an area made by a softer and more flexible material.

In a third preferred embodiment the at least one flexible area is constructed of an area made of a material which by its form has an ability for extension and compression such as a material being pleated or folded.

Preferably the injection part and the delivery part are not connected to each other by non-flexible or rigid areas as this would reduce the effect of the flexible areas. That the injection part and the delivery part are not connected to each other by non-flexible or rigid areas means that only flexible areas connect the injection part and the delivery parts.

In a preferred embodiment the device comprises a base part fastened to the patient's skin, the delivery part is fastened to a first part of the base part and the injection part is fastened to a second part of the base part, one or more flexible areas are positioned between the first part and the second part of the base part. Preferably the delivery part is releasably fastened to the base part, and the connector is unreleasably fastened to the base part. Also the connector is preferably fastened to the first part of the base part and more preferred the connector is fastened unreleasably to the first part of the base part with a non-flexible connection. In the described embodiments the base part is illustrated as a relatively flat part but the "base part" could be any construction which makes it possible to unite or combine the injection part and the delivery part into one unit which unit can be worn by the user directly fastened to the skin.

When the flexible areas are placed between the relatively heavy delivery device and the injection device, the transferal of actions from the delivery device to the injection device is prevented or at least significantly reduced, and the injection site of the subcutaneously placed cannula will be protected from the main part of any interaction resulting from pushing or touching the delivery part. Often the delivery part is separated physically from the injection part by a relatively long tube which prevents the transferal of actions but when the delivery part is positioned together with the injection device, the user will feel less discomfort when wearing a device according to the invention. By using a connector it is possible to avoid the direct contact between the delivery part and the injection part and at the same time fastened both parts as one unit to the skin of the user.

The cannula can protrude from the proximal side of the body of the injection part or from the side of the body. If the cannula protrudes from the side of the body as it does in the embodiments shown in FIG. 4 and FIG. 7, the cannula will normally be bending and it would be preferred to use a cannula which is at least partly formed of a soft and flexible material. If the cannula protrudes from the proximal side of the body as shown in FIG. 12, the cannula can be made of a hard material such as metal or it can be made of a soft and flexible material.

According to the invention the connector needle can be one end of a single needle which at the other end functions as the cannula. When the connector needle and the cannula is formed as one needle it will normally be made of metal or hard polymer but it can also be made of e.g. a polymer which is hardened in the connector end and unhardened and soft in the cannula end. Also the single needle can be composed of two different materials, a hard material for the connector end and a relatively soft material for the cannula end. Also the connector needle and the cannula can be separated into at least two needles. The injector part can then be provided with a commonly known soft cannula which cannula can be inserted by the help of an insertion needle attached to a separate inserter, and the connector needle can be made of a hard material and fastened to either the injector part or the delivery part.

The flexible areas are constructed of an area with reduced material dimensions, e.g. openings or cuts can be provided in a material or the thickness of a material can be reduced, or of an area made by a softer and more flexible material or it is constructed of an area made of a material which by its form or structure has ability for extension and compression such as a material being pleated or folded.

Preferably access of micro organisms to the reservoir during a non-connected state, i.e. when the reservoir and the injection part are separated, is prevented as the opening to the reservoir is blocked when the two parts separate.

The word "passing" comprise all possible ways to make a flow pass through or around a barrier, in most of the embodiments of this invention the barrier is passed by penetrating the barrier with a needle but there is also an example (FIGS. 18A and B) where the barrier is passed by pushing aside a hard cover thereby creating a flow path.

If the barriers comprise a material which can be penetrated by a needlelike object, the opening close on retraction of the needle like object. The needlelike object can be either blunt or sharp-pointed meaning that the needlelike object either pushes its way through the barrier or cuts its way through the barrier. If one of the barriers comprises a hard surface, i.e. a non-penetrable surface, the barrier will have to be moved in order to form an opening in the area positioned between the outlet of the outlet pipe and the inlet of the through going fluid path.

In a most preferred embodiment the device is fastened to the patients skin by applying a mounting pad adhered to the proximal side of the base part or to the proximal side of the infusion part, the adhering of the mounting pad to the base part or infusion part can include glue, Velcro, moulding etc.

Embodiments of the invention will now be described with reference to the figures in which:

FIG. 20 shows a sixth embodiment having a base part equipped with a central connector and peripheral injection part.

FIG. 21 shows the delivery device and the base part of the sixth embodiment in a joined state from above and from the side.

FIG. 27 shows the delivery device and the base part of the seventh embodiment in a joined state from the side and from above.

FIG. 28 shows a cut through view of the seventh embodiment in the joined state of FIG. 27 and an enlargement of the combined connector/injection part.

Figure 1:
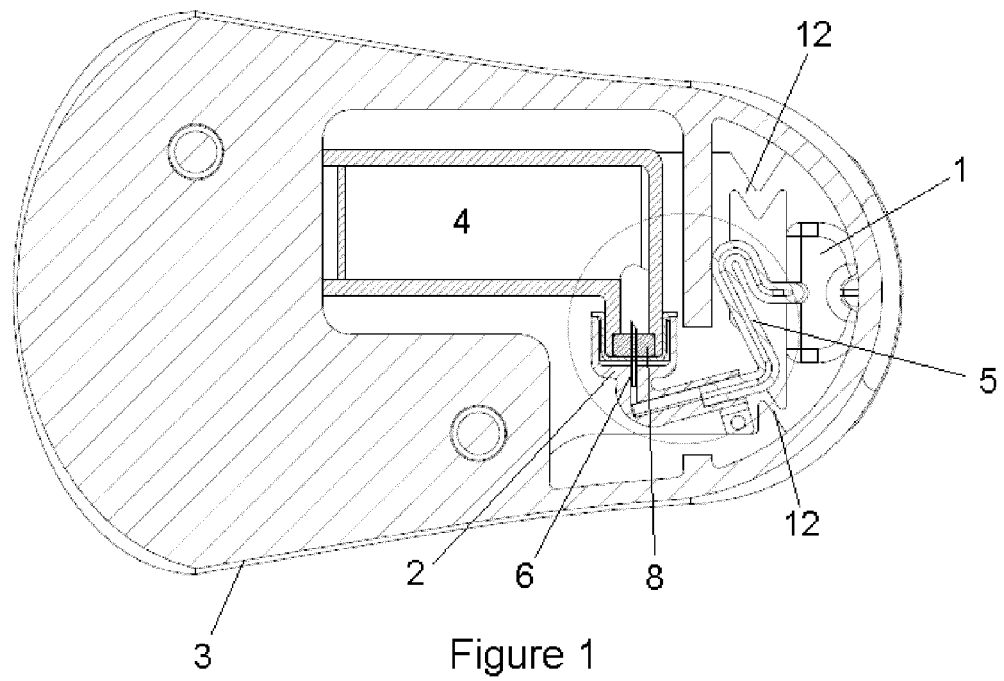
FIG. 1 shows a first embodiment of the invention from above at the B-B line shown in FIG. 3, where the delivery part is placed beside the injection part.
Figure 2:
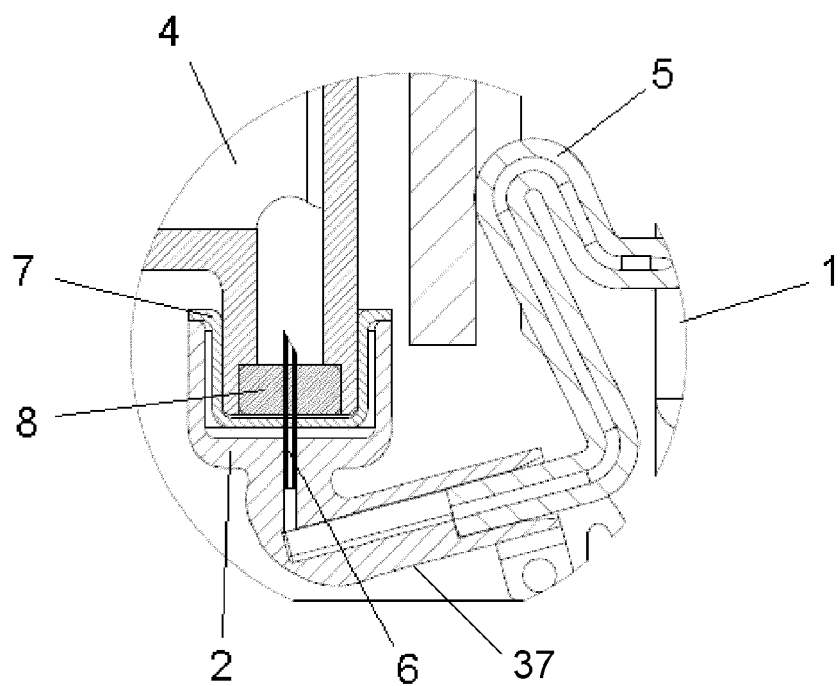
FIG. 2 shows an enlarged part, marked with a circle, of the embodiment in FIG. 1.
Figure 3:
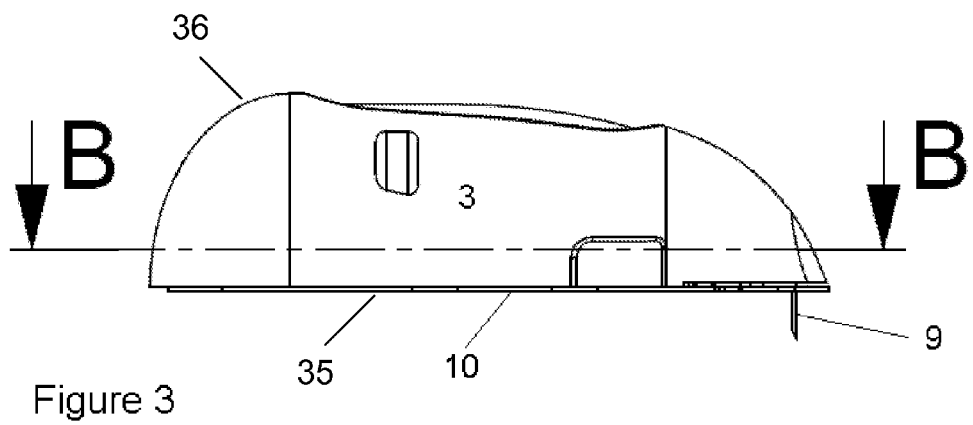
FIG. 3 shows the embodiment of FIG. 1 from the side indicating the line B-B.

FIG. 1-3 show a first embodiment of the invention where the delivery part and the injection part are fastened to each other. In FIG. 1 the embodiment is seen from above at the B-B line shown in FIG. 3 and FIG. 2 show a small part of FIG. 1 in enlarge form. The device comprises an injection part 1, a connector 2, a delivery part comprising a pump 3 and a reservoir 4, a flexible tube 5 creating a fluid connection between the injection part 1 and the delivery part, a connector needle 6 which can penetrate both a protective seal 7 covering the entrance of the connector and a septum 8 covering the entrance of the reservoir and a cannula 9 which is placed subcutaneously during use. In FIG. 1-3 the device is in a connected state where the injection part and the delivery part are joined together and ready for use.

FIG. 2 shows an enlargement of the connector 2 of FIG. 1. In this embodiment the connector 2 comprises a molded part 37 in a non-flexible material with a through-going opening which in one end is connected to the flexible tube 5 and in the other end is provided with a connector needle 6. In a state where the connector 2 is not connected to the reservoir 4, the connector needle 6 extends into a closed room comprising walls formed respectively of a cylindrical extension of the connector 2 and of the elastic protective seal 7. In the connected state the protective seal 7 is pushed towards the inside wall of the connector 2 surrounding the connector needle 6 and when connecting the connector 2 to the reservoir 4 the connector needle 6 first penetrates the protective seal 7 and then the septum 8 in order to create a passage from the connector 2 to the inside of the reservoir 4. In this embodiment the connector 2 is fastened unreleasably to a base plate which is an integrated part of the delivery part 3, 4.

FIG. 3 shows the embodiment of FIG. 1 from the side as it would look when the device is in use. A base plate 10 is placed along the skin of the patient and fastened to the patient e.g. by an adhesive pad 35. The cannula 9 protrudes from the proximal side of the base plate below the injection part 1 and injection part is covered by a housing part. The delivery part 3, 4 is fastened to the distal side of the base plate 10 beside the injection part 1 and is also covered with a housing part 36.

The base plate 10 will normally at the proximal side be fastened to the patient by an adhesive part or layer but any kind of mounting which will make the base plate stick to the patient without allowing the device to move can be used. The adhesive part or layer can be fastened to the base plate 10 by glue, Velcro, molding or the like.

In a preferred embodiment the delivery part is fastened to the distal side of the base plate 10 by one or more magnets which are embedded in the base plate 10. The detachable delivery part has corresponding magnets which keeps the delivery part in position during use. By means of the magnets of the base plate 10 and/or the delivery part 3, 4 it will be possible to detect conditions of the system such as whether the delivery part is secured properly, if the flow through the device is OK, how long has the delivery part been fastened to the base plate, size of the volume which has passed the device, etc.

Figure 4:
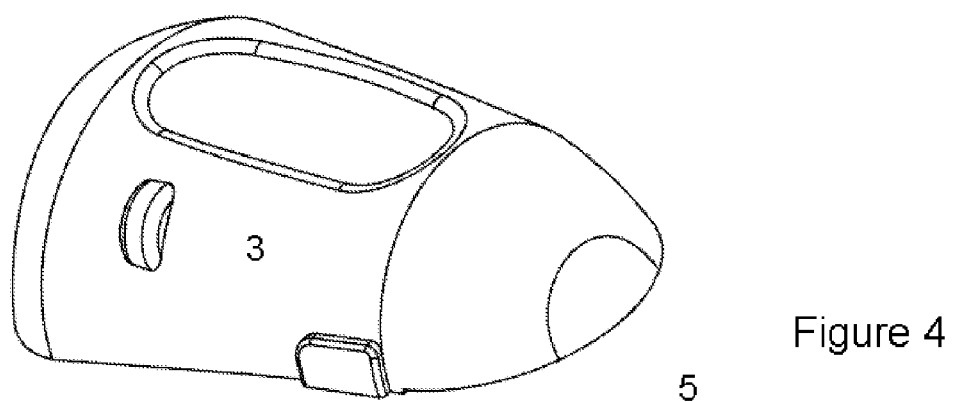
FIG. 4 shows the first embodiment where the delivery part is separated from the injection part.
Figure 4:
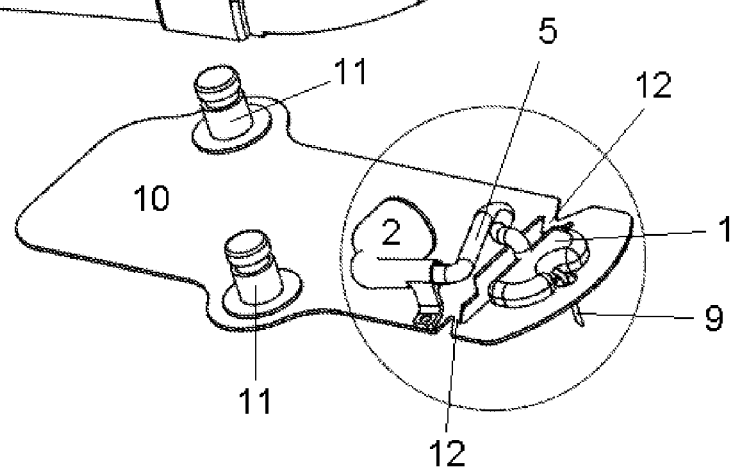

FIG. 4 shows the first embodiment in a separated state where it is possible to see the base plate 10 to which the injection part 1 is fastened, objects 11 for fastening of the delivery part to the base part 10 and a flexible portion 12 of the base plate. In order to fastened the delivery part to the base part 10 the delivery part 3, 4 is pushed down towards the base part 10 from above. The flexible portion 12 is constructed of two thin connections formed as straight lines and made by removing material from the plane of the base part 10. This construction of the base part 10 together with the flexible tube 5 allows the injection part 1 which is attached to the cannula 9 to remain in a stationary position although the part of the base part 10 to which the delivery part is fastened is touched or pushed or just moves as a result of the movements of the user.

Figure 5:
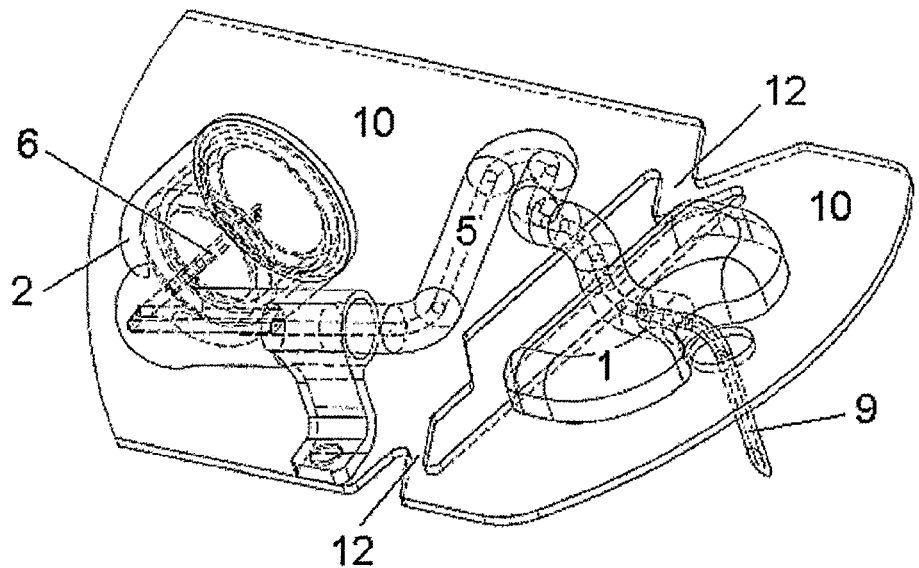
FIG. 5 shows an enlarged part, marked with a circle, of the embodiment in FIG. 4.

FIG. 5 shows an enlargement of a part of the first embodiment of FIG. 4. FIG. 5 shows in greater detail how the cannula 9 is held in position by the injection part 1; the injection part 1 via the flexible tube 5 is connected to the connector 2. The connector 2, which is fastened to the base part 10 on the same side of the base part 10 as the delivery part, is shown in a transparent form which makes it possible to see the connector needle 6. The connector 2 is preferably made of PP, ABS or similar materials.

In the first embodiment described in FIG. 1-5 one of the flexible areas between the delivery part 3, 4 and the injection part 1 is formed by the flexible tube 5. The flexible tube can be produced as a piece of extruded tube, and can be made of PUR (polyurethane), PP (polypropylene), PE (polyethylene), silicone or any other material which is adequately flexible or can be brought into a flexible form e.g. by providing the tube with folding.

The cannula 9 which is integrated with the infusion part 1 and fastened unreleasably to the base part 10 can be inserted subcutaneously either by the help of an inserter or manually.

The house of the delivery part 3, 4 is made of a relatively hard material such as PP or ABS (Poly (Acrylonitrile, Butadiene, Styrene)) which makes it possible for the house to resist impacts of the surroundings.

Figure 6A:
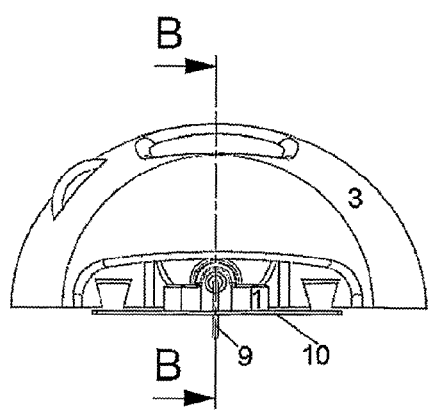
FIG. 6A shows a second embodiment of the invention seen from the side of the injection part.
Figure 6B:
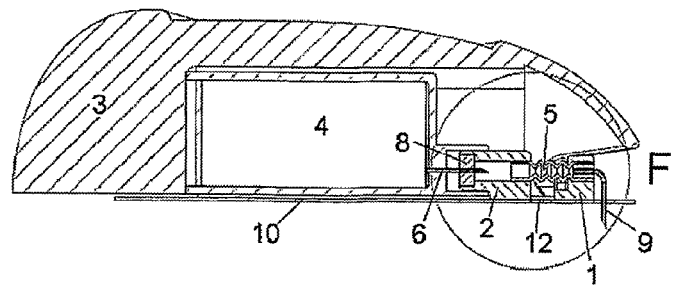
FIG. 6B shows the same embodiment as in FIG. 6A seen from the cut made by the line B-B.
Figure 7:
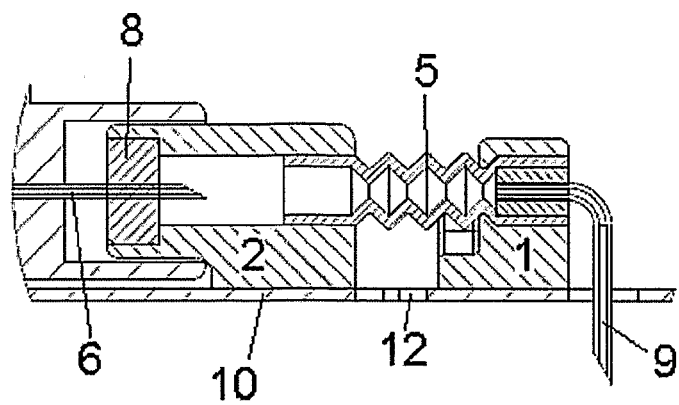
FIG. 7 shows an enlarged part, marked with a circle, of the embodiment in FIG. 6B.

FIG. 6A shows a second embodiment of the device for delivering fluid according to the invention seen from the side facing the injection part. FIG. 6B shows the same embodiment seen from a cut through the device at the line B-B. FIG. 7 shows an enlargement of the part of the embodiment connecting the injection part 1 to the delivery part 3, 4 through the connector 2. In FIGS. 6A, 6B and 7 the delivery part and the injection part are both connected to the base part 10 which is the state of the device when in use.

In the second embodiment the injection part 1 is connected to the delivery part 3, 4 by a flexible tube 5 which in this embodiment is formed as a bellows and preferably is made of silicone, PUR, PP/PE or the like. The flexible portions 12 of the base part 10 is formed as relatively thin V-shaped connections made by removing material from the plane of the base part 10. The flexible portions 12 can also be constructed of another material e.g. TPE: This embodiment is provided with sliding rails 11 acting as objects for fastening of the delivery part 3, 4 to the base part 10. In this embodiment the connector needle 6 is fastened to the delivery part 3, 4. The connector needle 6 penetrates a septum 8 when the delivery part is joined to the connector 2 and thereby creates a flow path from the reservoir 4 to the cannula 9.

Figures 8A, 8B:
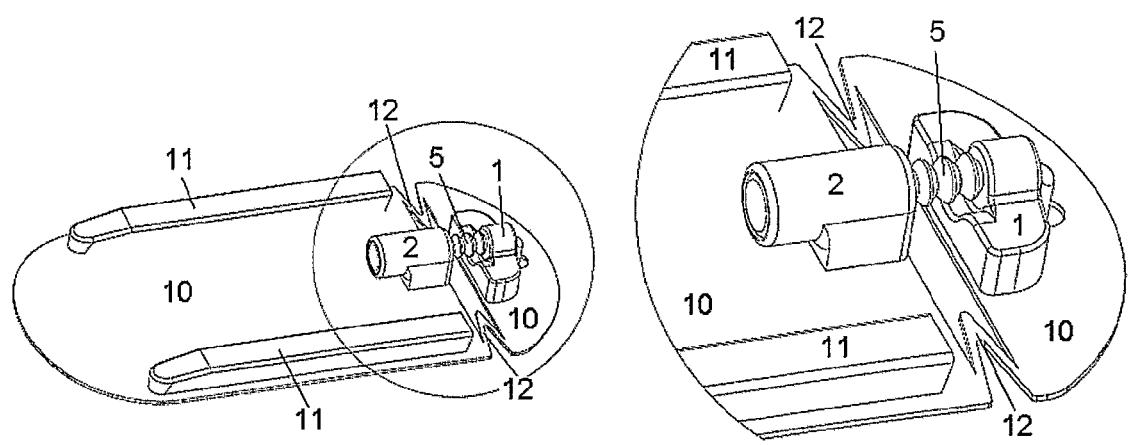
FIG. 8A shows the injection part and the base part of the second embodiment separated from the delivery part.
FIG. 8B shows an enlarged part, marked with a circle, of the embodiment in FIG. 8A.

FIGS. 8A and 8B shows the embodiment in a state where the delivery part 3, 4 is separated from the base part 10 which makes it possible to see the two sliding rails 11.

In FIG. 8B is shown an enlargement of the connector 2 of FIG. 8A. In this embodiment the connector 2 comprises a molded part in a non-flexible material with a through-going opening which in one end is connected to the flexible tube 5 and in the other end is provided with a septum 8. The flexibility of the flexible tube 5 can be obtained be using a soft and flexible material but in this embodiment the flexibility of the tube 5 is obtained by constructing the flexible tube 5 of a stable—that is a rather rigid—and corrugated material. The reservoir 4 is provided with a connector needle 6 and a cylindrical extension which extension protects the connector needle 6 and can be provided with a protective seal (not shown in FIG. 8B). In a state where the connector 2 is not connected to the reservoir 4, the connector needle 6 extends into a closed room comprising walls formed of the cylindrical extension of the reservoir 4 and possibly of an elastic protective seal. In the connected state the protective seal if present is pushed towards the inside wall of the reservoir 4 surrounding the connector needle 6 and when connecting the connector 2 to the reservoir 4 the connector needle 6 first penetrates the protective seal and then the septum 8 in order to create a passage from the reservoir 4 to the inside of the connector 2. In this embodiment the connector 2 is fastened unreleasably to the base plate 10 which is an integrated part of the delivery part 3, 4.

Figure 9:
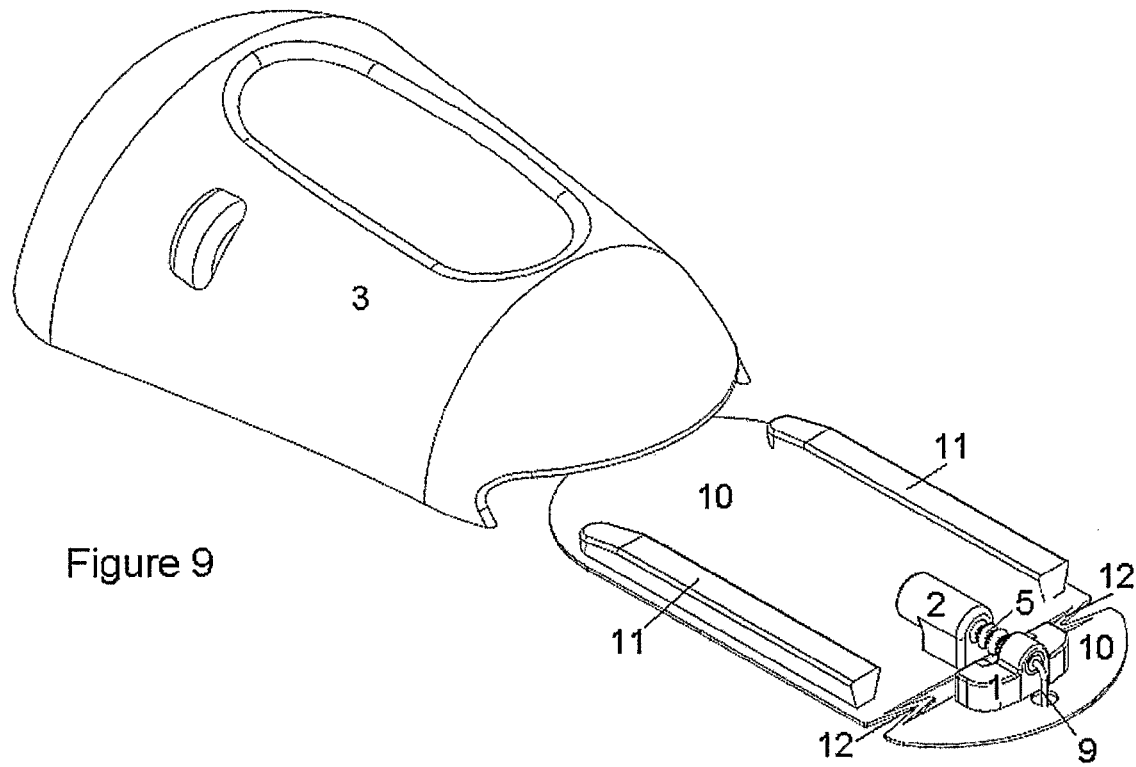
FIG. 9 shows both the delivery part and the injection part of the second embodiment.
Figure 10A:
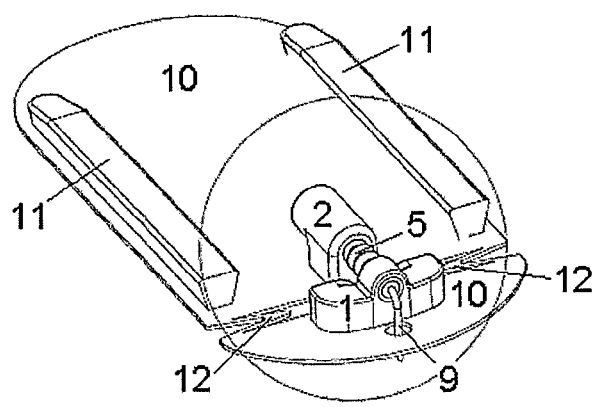
FIG. 10A shows the same embodiment as FIG. 8A from a different angle.
Figure 10B:
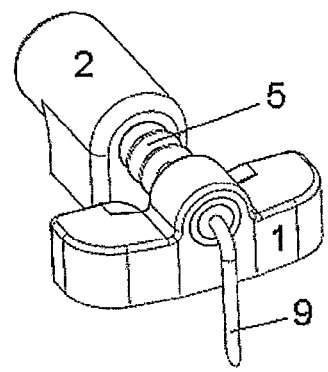
FIG. 10B shows an enlarged part, marked with a circle, of the embodiment in FIG. 10A.

FIGS. 9, 10A and 10B also show the device according to the second embodiment of the invention. FIG. 9 shows the delivery part 3, the base part 1 and the injection part 1 and how they are positioned relatively to each other just before they are being joined and an arrow indicates the direction of movement when the delivery device 3, 4 is fastened to the objects 11 of the base part 10 in order to form a connection to the injection part 1. FIG. 10A shows the same embodiment as FIG. 8A from a different angle and FIG. 10B shows an enlargement of the connector 2, marked with a circle, of the embodiment in FIG. 10A. In this embodiment the cannula 9 protrudes laterally from the injector device and has been inserted perpendicularly to the users' skin. If the cannula 9 is made of a soft and flexible material it is necessary to use an insertion needle to penetrate the skin of the user. This can be done manually by providing the device with an insertion needle protruding through the proximal opening of the cannula 9. The sharp insertion needle exits from the proximal end of the cannula 9 and it is either entering the distal end of the cannula, e.g. through a septum covering the distal opening of the cannula 9, or it is entering the cannula through the side. In case the insertion needle enters the cannula 9 through the side it is necessary to provide the entering position with some kind of a closure in order to prevent micro organisms to enter the device when the insertion needle is removed after insertion. This embodiment of the device can be inserted with an inserter e.g. the inserter known from PCT application no. DK2005/050010 filed on Dec. 9, 2005. If the cannula was protruding from the proximal side of the injection part it could e.g. have been inserted with the inserter known from PCT application DK02/00640 filed on Sep. 27, 2002.

Figure 11:
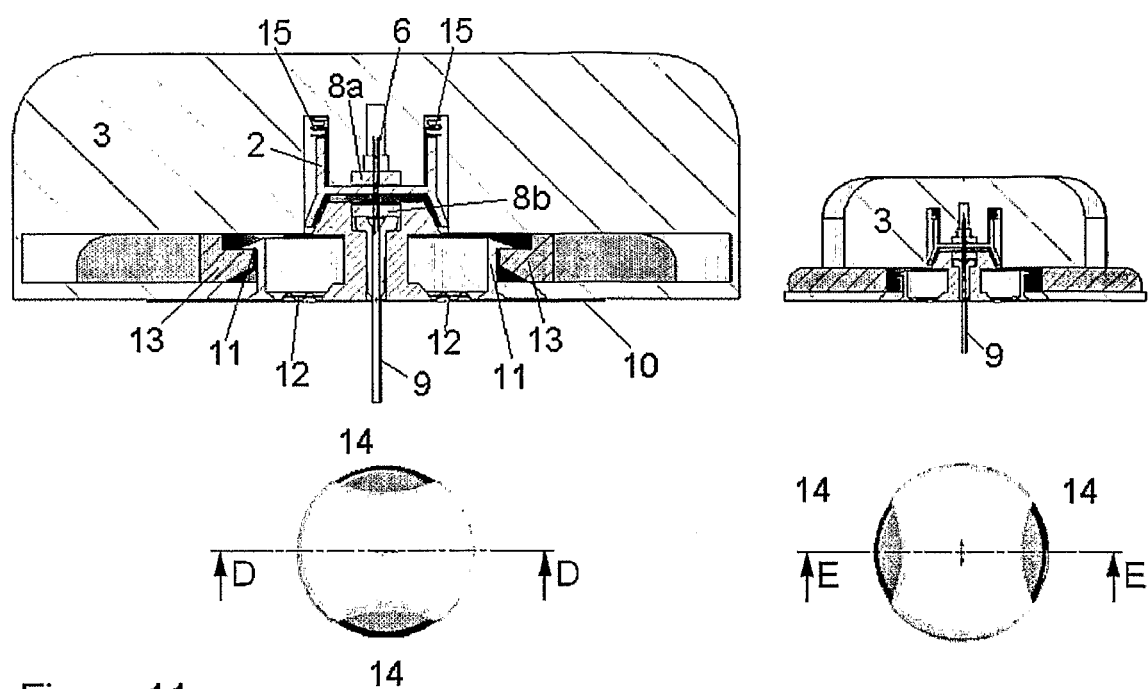
FIG. 11 shows a third embodiment of a delivery device according to the invention in a connected state, and in this embodiment the delivery part is placed on top of the injection part.

FIG. 11 illustrates an embodiment where the delivery part 3, 4 is placed on top of the injection part 1. In this embodiment the delivery part is fastened releasably to a portion of the base part 10 which surrounds the injection part 1. The flexible portion 12 of the base part placed around the injection part is formed as a circular folded material which is either the same material as the central part of the injection part in a thinner form or of a different material of a more soft or flexible nature. In FIG. 11 the delivery part 3, 4 and the injection part are joined together as they would be when the device is in use and a connection which allows for fluid to flow from the reservoir to the cannula 9 is formed. The left and the right versions show views of two different cuts along the lines D-D and E-E respectively at perpendicular angels through the device. In this embodiment the objects 11 for fastening of the delivery part 3, 4 to the injection part are formed as circular profiles standing upright from the base part 10 and having an outward projection which objects 11 fit with corresponding projections 13 on the delivery part. When the delivery part 3, 4 is to be fastened to the injection part 1 two handle portions 14 are pushed together which makes the corresponding projection move outwards and allow the injection part to enter the central opening in the delivery part 3, 4. When the user lets go of the handle portions 14 the corresponding parts return to the more central position and locks the injection part 1 to the central opening of the delivery part 3, 4.

The delivery part 3, 4 is combined with a connector 2; the connector 2 has a through-going connector needle 6 and is influenced by a spring 15. When the user pushes the delivery part 3, 4 towards the injection part 1, the spring 15 is compressed and the through-going connector needle 6 is forced through a septum 8a protecting the content of the reservoir from being infected with micro organisms. At the same time or just before or afterwards the connector needle 6 will also be forced through a septum 8b protecting the access to the cannula 9 thereby forming a fluid connection between the not shown reservoir and the cannula 9. By choosing convenient materials for the spring 15, the septum 8a and other materials being in contact with the connector 2, it should be assured that there exists a flexible connection between the connector 2 and the delivery part 3, 4. Preferably the connector 2 is fastened to the spring 15 while the movement from one position to another is guided by the walls of the central extension of the delivery part 3, 4, and the septum 8a is made of a material which is adequately soft to assure that the connector 2 is flexibly connected to the delivery part 3, 4 when the device is in a connected state. In this embodiment the connector 2 does not have to be fastened to neither the delivery part 3, 4 nor the injector part 1, the connector 2 can be a separate unit which functions as an independent interface or it can be integrated with either the delivery part 3, 4 or the injection part 1.

Figure 12:
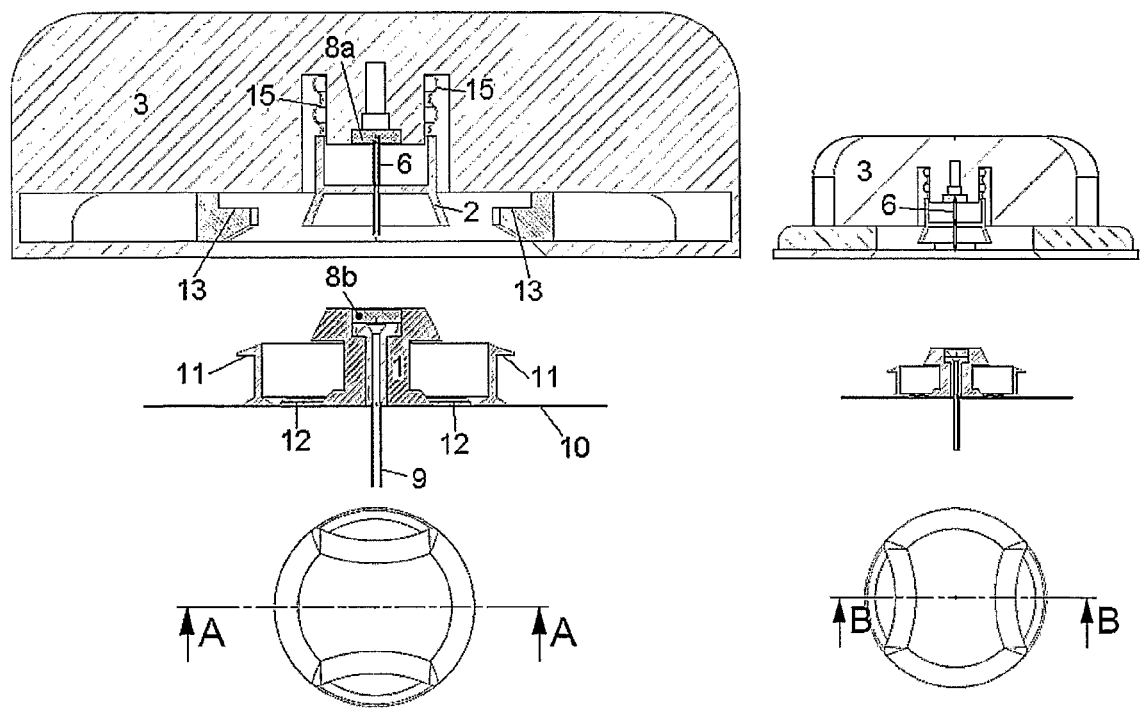
FIG. 12 shows the third embodiment of the device in a separated state.

In FIG. 12 the embodiment of FIG. 11 is shown in a state where the injection part 1 is separated from the delivery part 3, 4 which leaves the spring 15 in a relaxed and extended state. In this state the through-going connector needle 6 has neither penetrated the septum 8a of the delivery part 3, 4 or the septum 8b of the injection part 1.

Figure 13:
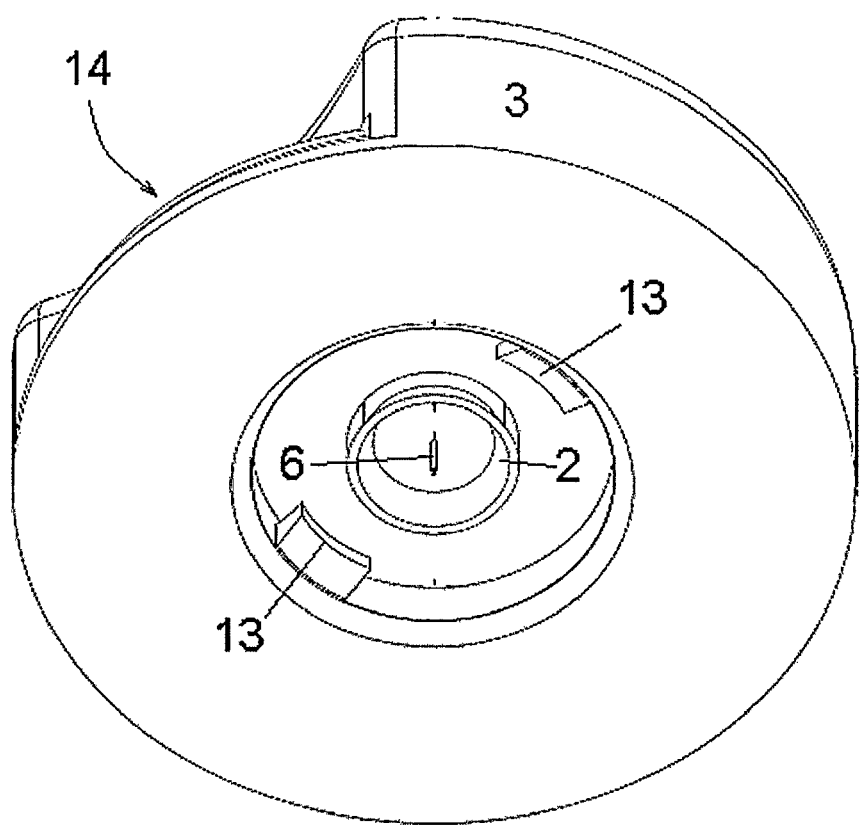
FIG. 13 shows the two parts of the third embodiment from the upper and lower side respectively.
Figure 13:
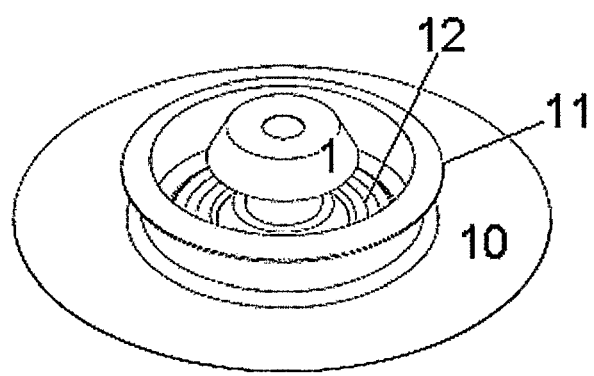

FIG. 13 shows the embodiment of FIGS. 11 and 12 in a three dimensional form. The delivery part 3, 4 and the injection part 1 joined to the base part 10 are shown from the sides where the two parts correspond to each other when joined.

The embodiment shown in FIG. 11-13 can be inserted with an inserter of the type known from PCT application DK02/00640 filed on Sep. 27, 2002. After insertion of the injection part 1, the user fastened the base part 10 to the skin. With the injection part 1 in position the user can then fastened the delivery part comprising at least one reservoir and transferring means preferably in the form of a pump to the injection part 1. If the connector 2 has the form of a separate interface the connector should be placed before the delivery part 3, 4 is fastened to the injection part and the connector will then provide for a proper fitting between the chosen injection part 1 and the chosen delivery part 3, 4.

When introducing the flexible areas as described in FIG. 1-13 and as claimed it will be possible to move the releasable delivery part 3, 4 in all dimensions within certain boundaries defined by the size of the used parts as it will be possible to pull, push, lift and move the delivery part 3, 4 side wards without influencing the cannula 9 and disturbing the insertion site which would normally result in discomfort to the patient.

All the embodiments containing need to be fastened to the patients skin and this is preferably done by applying a mounting pad adhered to the proximal side of the base part 10 or to the proximal side of the infusion part 1 if the embodiment is not provided with a base part 10. The adhering of the mounting pad to the base part 10 or infusion part 1 can include glue, Velcro, moulding etc.

Figure 14:
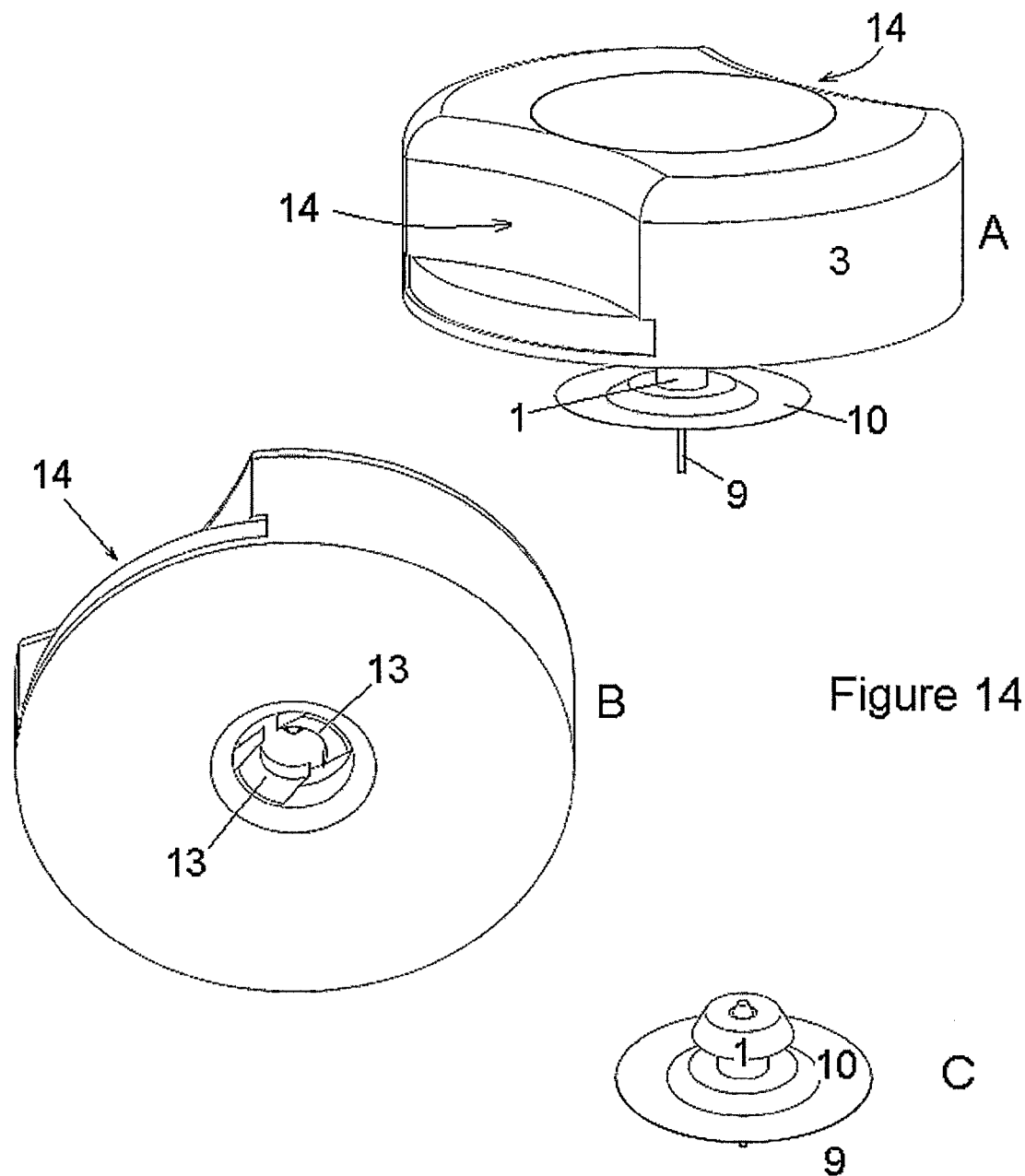
FIG. 14 shows a fourth embodiment of the delivery device according to the invention. "A" shows the delivery part with the injection part prepared to be connected with the delivery part seen from the side, "B" shows the delivery part from beyond and "C" shows the injection part seen from above.

FIG. 14 shows an embodiment according to which it is possible to assure a fluid tight transferal of fluid from the reservoir in the delivery part 3, 4 to the cannula 9 of the injection part 1 and thereby to the patient.

In FIG. 14 "A" shows the device comprising both the delivery part 3, 4 and the injection part 1 seen from the side in a three dimensional form, "B" shows the delivery part 3, 4 from below in a three dimensional form and "C" shows the injection part 1 seen from above in a three dimensional form.

Figure 15:
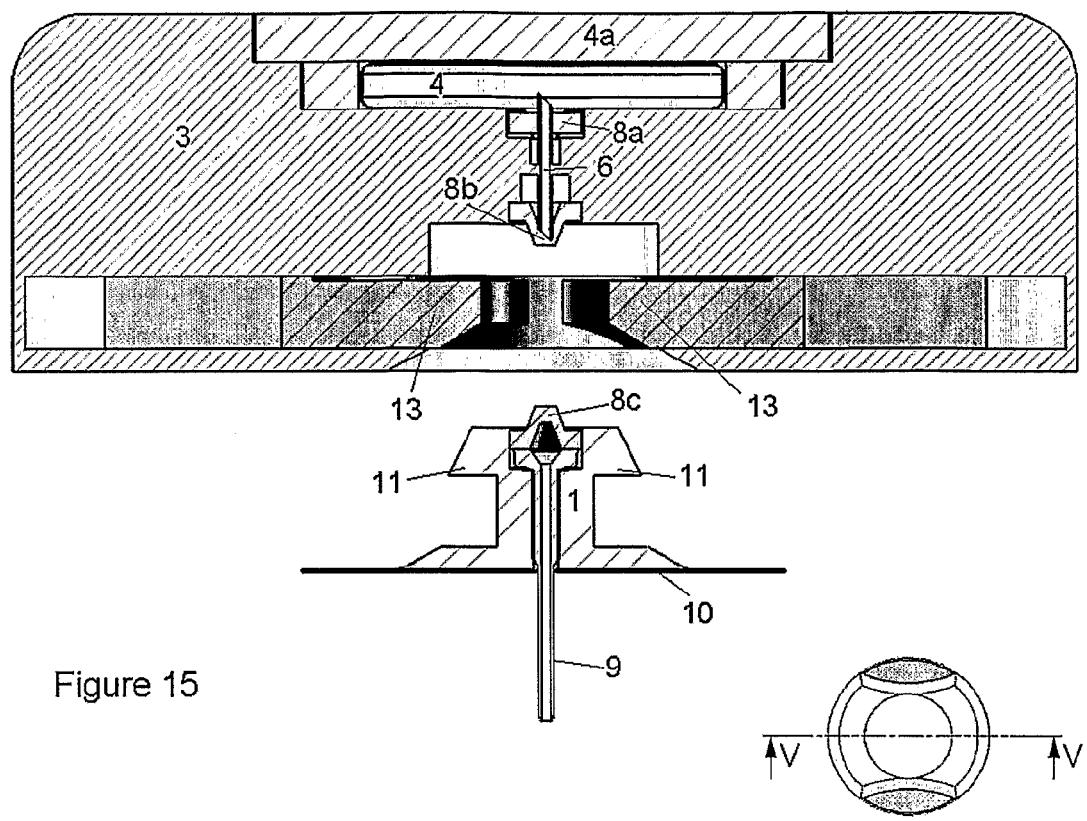
FIG. 15 shows the fourth embodiment seen from the side (line V-V) in a separated state.

FIG. 15 shows the same embodiment as in FIG. 14 and is a side view of the cut illustrated by the line V-V. In FIG. 15 the delivery part 3, 4 and the injection part are separated and the connector needle 6 is protected by a downward septum 8b preventing bacteria to enter the reservoir from this end. The septum 8a protecting the entrance of the reservoir is penetrated by the other end of the connector needle 6. In FIG. 15 is the reservoir 4 shown positioned above the connector needle 6 and above the reservoir 4 is a reservoir lid 4a shown. The reservoir lid 4a can be removed when e.g. an ampoule constituting the reservoir 4 has to be changed. In this embodiment the reservoir 4 has flexible walls and is surrounded by a ring 16 with which it is possible to reduce the volume of the reservoir and thereby pump fluid from the reservoir 4 to the patient. In this embodiment the injection part 1 is also provided with objects 11 for fastening of the delivery part 3, 4 to the injection part formed as a circular profile standing upright from the base part 10 and being integrated with the outer surface of the housing of the injection part 1. The outward projection of the objects 11 fit with corresponding projections 13 on the delivery part 3, 4. When the delivery part 3, 4 is to be fastened to the injection part 1 the two handle portions 14 are pushed together forcing the corresponding projections 13 outwards and allowing the injection part 1 to enter the central opening in the delivery part 3, 4. When the user let go of the handle portions 14 the corresponding parts 13 return to the more central position and locks the injection part 1 to the central opening of the delivery part 3, 4.

Figure 16:
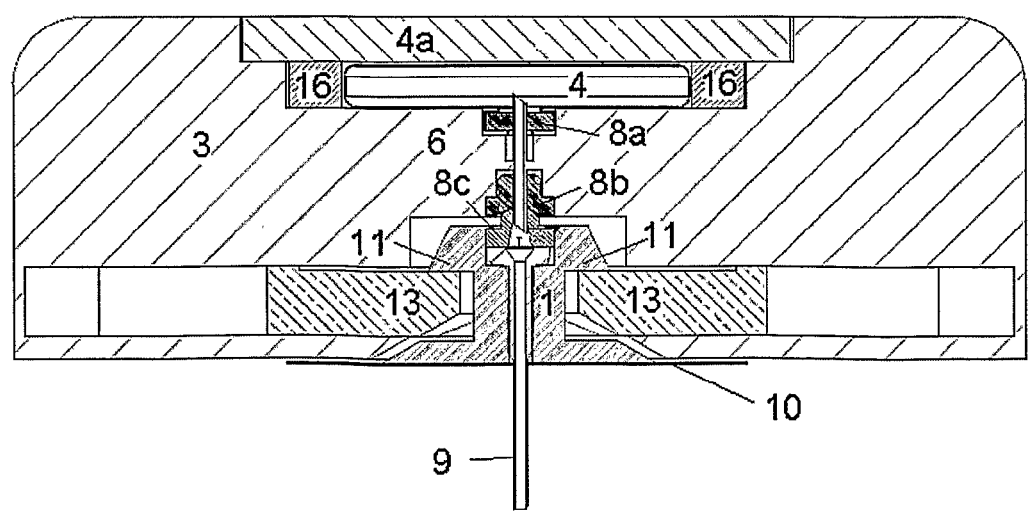
FIG. 16 shows the fourth embodiment seen from the side (line V-V) in a connected state.

FIG. 16 shows the same embodiment as in FIGS. 14 and 15 but in FIG. 16 the delivery part 3, 4 and the injection part 1 are joined together as they would be during use. In this position the connector needle 6 has penetrated all three septums 8a, 8b and 8c and has created a fluid connection between the reservoir 4 and the injection part 1.

Figure 17:
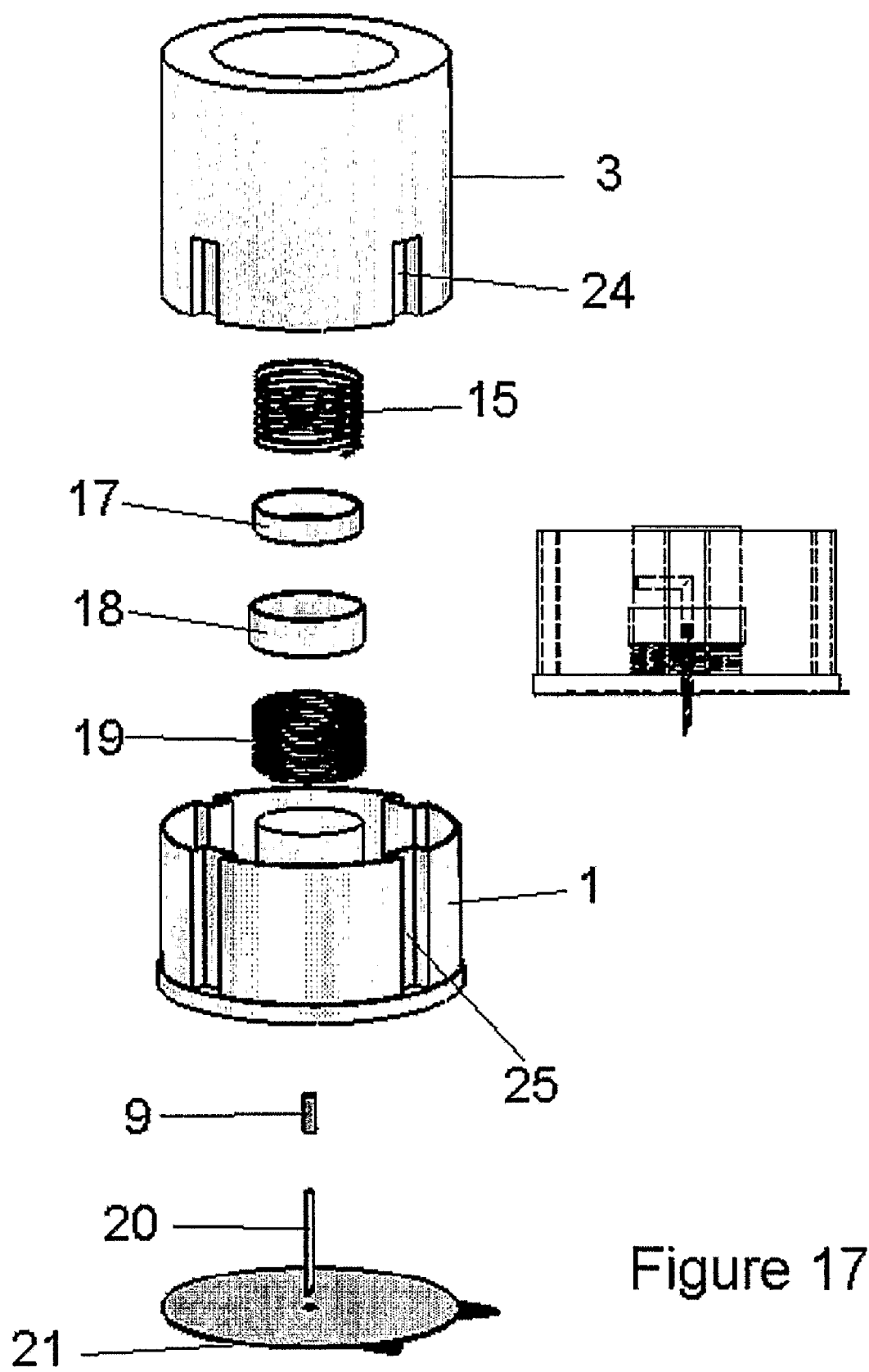
FIG. 17 shows a fifth embodiment of the delivery device according to the invention having a fluid tight lock between the delivery part and the injection part.

FIG. 17 shows an exploded view of an embodiment of a device according to the invention comprising a second fluid tight connection between the reservoir of the delivery part 3, 4 and the injection part 1. This embodiment comprises a delivery part comprising a pump 3 and a reservoir, a first spring 15, an upper packing 17, a lower packing 18, a second spring 19, an injection part 1, a cannula 9, an insertion needle 20 and a mounting pad 21. Further the outward surface of the delivery part 3, 4 is provided with grooves 24 and the outward surface of the injection part 1 is provided with corresponding tongues 25.

Figures 18A, 18B:
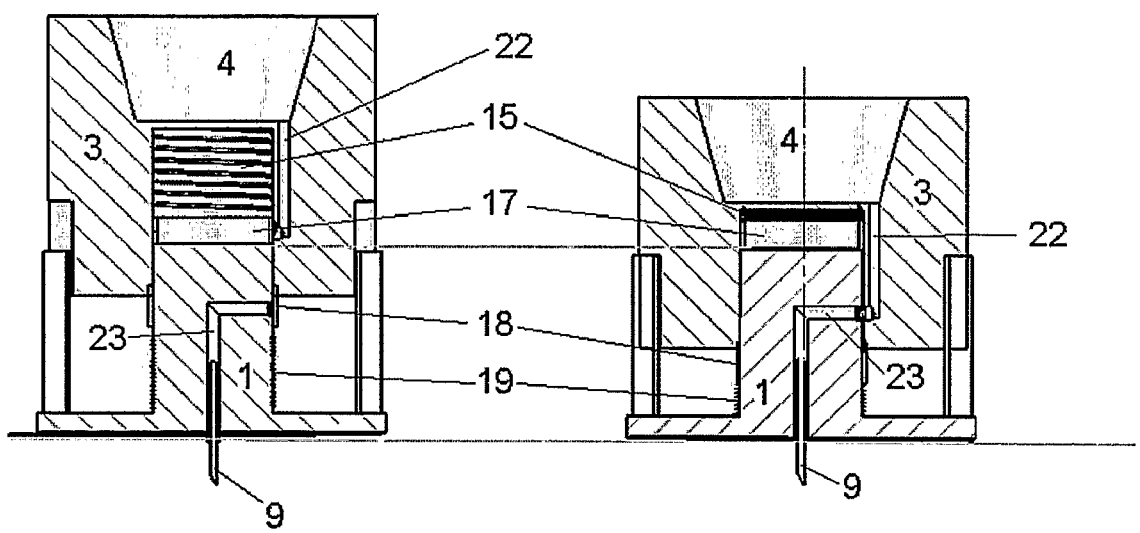
FIGS. 18A and 18B show an enlarged part of the fifth embodiment in two states; in the first state the device is closed for fluid flow, in the second state the device is open for fluid flow.

In FIG. 18 it is shown how the individual parts of the embodiment in FIG. 17 works together. In this figure the inside of the injection part and the delivery part 3, 4 is illustrated. In the delivery part 3, 4 is shown a possible placement of the reservoir 4 and an outlet pipe 22 from the reservoir 4. At the outlet end, in FIG. 18 the lowest end, the outlet pipe 22 is provided with a sideway directed opening and a packing which packing assures fluid tight contact between the wall of the central part of the injection part 1 and the outlet of the outlet pipe 22. The inside of the injection part 1 comprises a through-going fluid path 23 with an inlet opening sideways through the upright wall of the central part of the injection part 1.

In a first position the delivery part comprising the reservoir 4 and the pump 3 is retracted from the injection part 1, the first spring 15 is extended and the outlet from the outlet pipe 22 is blocked by the wall of the central part of the injection part 1. The lower packing 18 is in a high position where it blocks the inlet of the fluid path 23 and the second spring 19 is extended.

In a second position the delivery part 3, 4 is pushed towards the injection part 1 and both the first spring 15 and the second spring 19 are compressed. The lower packing 18, which in the first position functions as a barrier for bacteria, is pushed down by the lower edge of the delivery part 3, 4 and thereby opens the inlet of the fluid path 23. When the tongues 25 of the injection part 1 touch the upper side of the grooves 24 of the delivery part 3, 4 the downward movement of the delivery part stop and in this position the opening of the outlet pipe 22 corresponds to the inlet of the fluid path 23.

Figure 19:
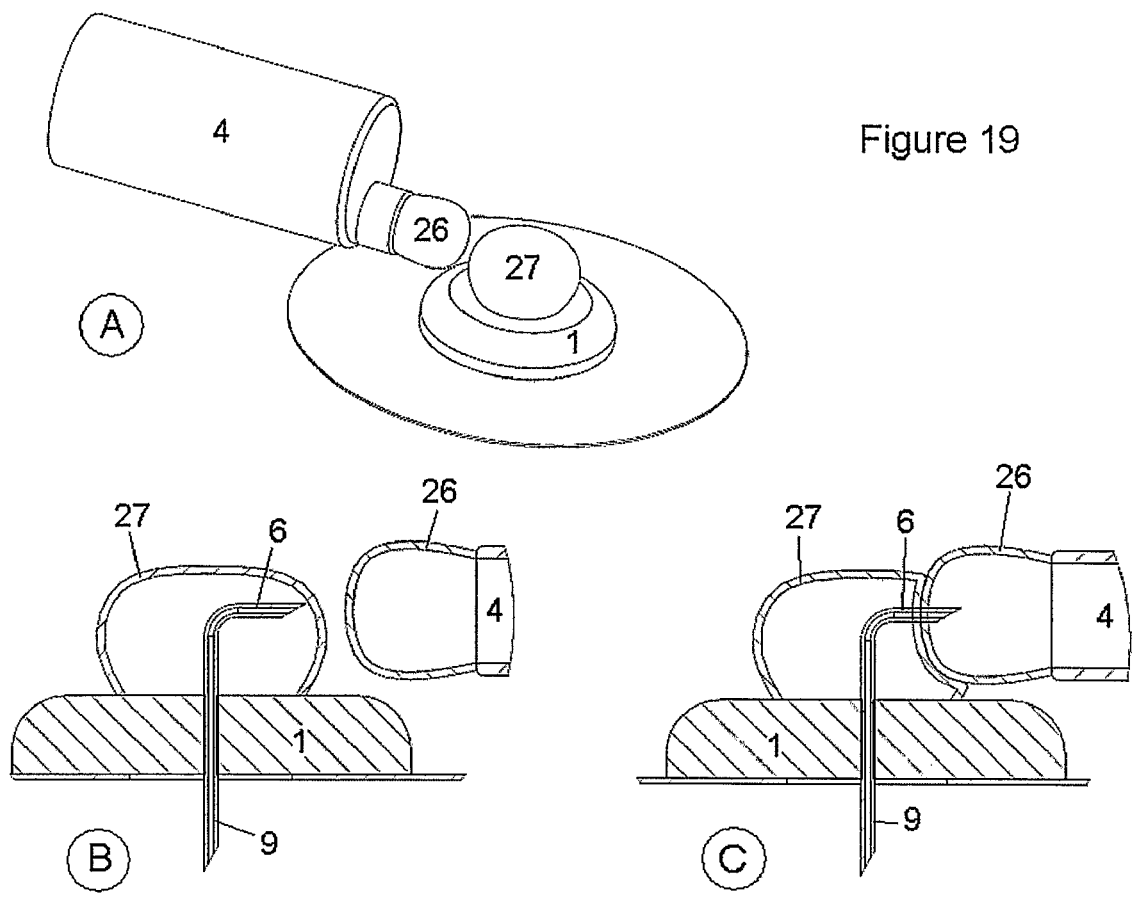
FIG. 19 shows another embodiment ensuring fluid tight transferal of fluid from the delivery part to the injection part.
Figure 22:
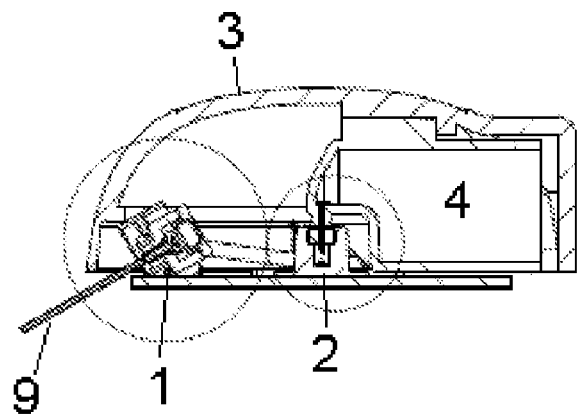
FIG. 22 shows a cut through view of the sixth embodiment in the joined state of FIG. 21.
Figure 23:
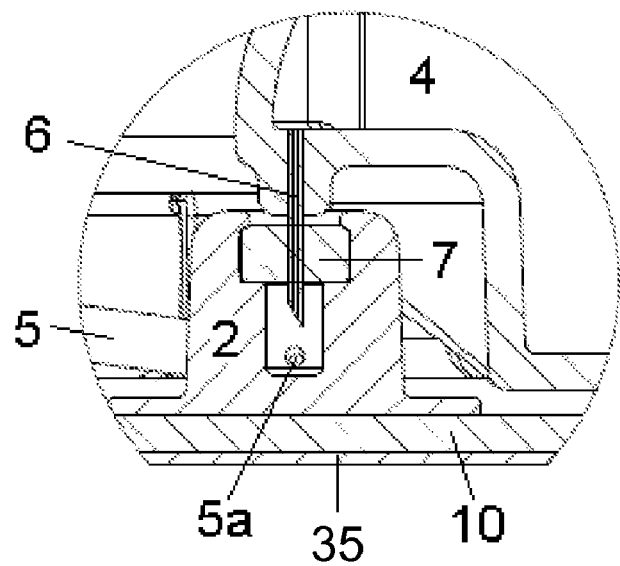
FIG. 23 shows an enlargement of the connector part of FIG. 22.

FIG. 19 shows another embodiment of a device according to the invention assuring a fluid tight connection between the reservoir and the injection part 1. This device comprises a delivery part 3, 4 e.g. as shown in FIG. 1-10 but only the reservoir 4 is shown in FIG. 19. The device is constructed of a reservoir where the outlet is covered by a bubble shaped deformable membrane 26; this membrane prevents that micro organisms access the reservoir when the delivery part is not joined to the injection part 1. That the membrane is bubble shaped means that the membrane not has flat inner and outer surfaces but has convex inner and outer surfaces, and that the membrane does not only cover the tip of the connector needle 6 but covers a larger part of the connector needle 6. The inlet of the injection part 1 is also covered by a deformable bubble shaped membrane 27. In this embodiment the connector needle 6 is fastened to the injection part 1 but the connector needle 6 could also be fastened to the delivery part 3, 4, if the connector needle 6 is fastened to the delivery part it is necessary to provide the combined device with two needles: a connector needle 6 and a cannula 9. If the device is provided with a connector needle 6 separate from the cannula 9 it is possible to use a soft cannula.

FIG. 19A shows a three dimensional view of the device in a state where the delivery part 3, 4 and the injection part 1 are separated and fluid can not flow between the two parts. FIG. 19B shows the same state as FIG. 19A but seen from a vertical cut through the device. In FIG. 19C the delivery part 3, 4 and the injection part 1 has been pushed together and the fluid of the reservoir 4 can now flow through the injection part 1 and the cannula 9 to the patient. When the two membranes are pushed together membranes are deformed and the pointy connector needle 6 penetrates both membranes and forms a fluid connection, it is possible to form each of the bubble shaped membranes 26 and 27 with a varying hardness in order to control where it is desirable to penetrate the membranes by using the varying hardness to shape a base for the least deformable membrane when it is pushed against the most deformable membrane.

The membranes 26 and 27 can be made of silicone or polyurethane (PUR) or other soft polymers which can be penetrated by a needle but not by micro organisms.

The connector needle 6 is made of a relatively hard material such as metal or a hard polymer, "a relatively hard material" means that the material should at least have the strength, i.e. be hard enough, to penetrate the membranes 26 and 27.

In the embodiment of FIGS. 19A, B and C the connector needle 6 is one end of a single needle which at the other end functions as the cannula 9. When the connector needle 6 and the cannula is formed as one needle it will normally be made of metal or hard polymer but it can also be made of e.g. a polymer which is hardened in the connector end and unhardened and soft in the cannula end. Also the single needle can be composed of two different materials, a hard material for the connector end and a relatively soft material for the cannula end.

It is also possible to separate the connector needle 6 and the cannula 9 and produce the device according to the invention with two needles. The injector part 1 can then be provided with a commonly known soft cannula which cannula can be inserted by the help of an insertion needle attached to a separate inserter, and the connector needle 6 is made of a hard material and fastened to either the injector part 1 or the delivery part 3, 4.

In this embodiment the single needle is bend, i.e. the connector needle 6 points in a direction parallel to the patients skin while the cannula 9 points in a direction perpendicular to the patients skin. According to the present invention the connector needle 6 can point in any direction parallel or away from the patient and the cannula 9 can point in any direction according to which the cannula can be inserted into the patient's skin.

The device according to the invention can be used in connection with all kinds of medicaments and all kind of conditions where patients can benefit from a continuous intake of a drug product; preferably it is the intention to provide patients suffering from diabetes with a secure and easy-to-handle device which can provide the patient with continuously regulated doses of insulin.

In a preferred embodiment the reservoir is divided into several separate chambers where each chamber can be provided with different drug products or e.g. an active drug substance in one chamber and a solvent in another chamber, the different chambers can contain drugs of different concentrations or drugs with different active substances.

FIG. 20-25 show an embodiment of the invention where the connector 2 has been placed in a central position of the base plate 10 and the injection part is fastened to a peripheral part of the base plate 10. The peripheral placement of the injection part makes it possible for the user to observe the injection site. Further the injection part of this embodiment is arranged in such a way that the cannula is to be injected at an angle A deviating from 90° in relation to the distal surface of the base plate 10, normally the angle A will be between 110° and 170° where the distal surface of the base plate 10 form one side of the angle and the inserted cannula form the other side of the angle.

In this embodiment the flexible portion 12 is constructed from the base plate 10 and formed like four spokes in a wheel. It is possible to vary the flexibility of the flexible portions 12 by varying the width of the portions 12, the thickness of the base plate material 10 or the number of portions 12 (spokes).

Figure 24:
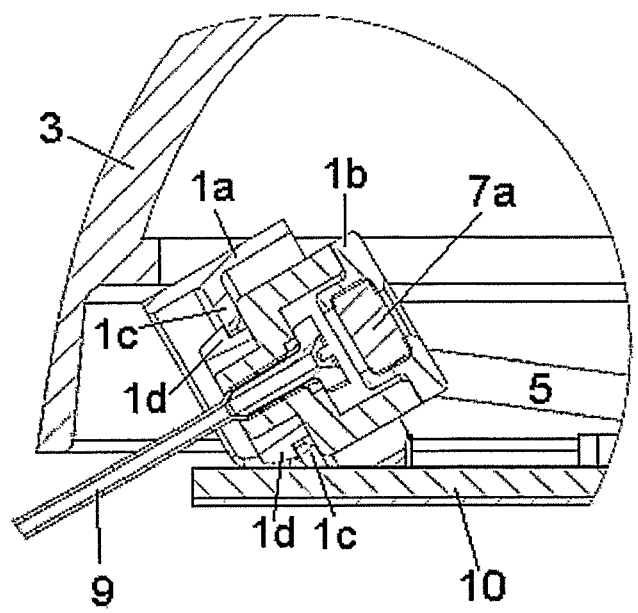
FIG. 24 shows an enlargement of the injector part of FIG. 22.
Figure 25:
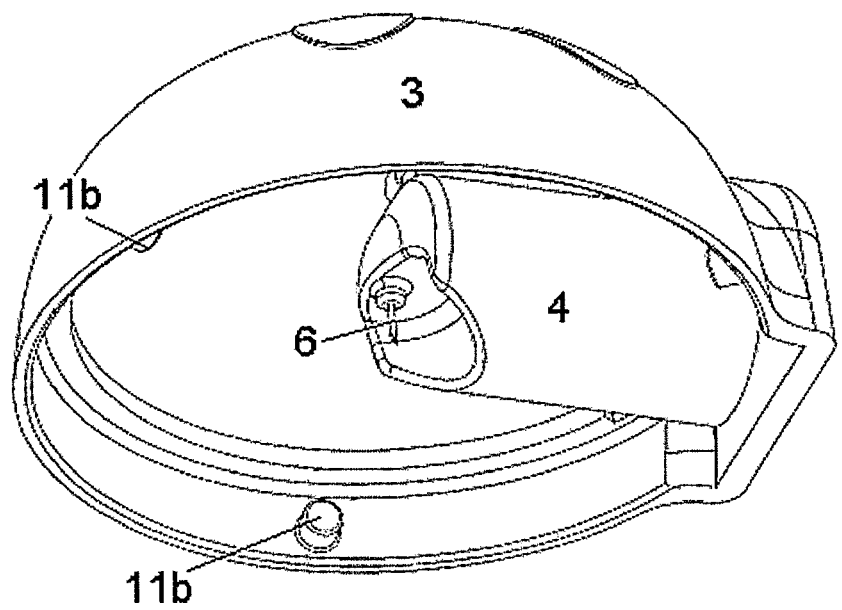
FIG. 25 shows a view from below of the delivery part of the sixth embodiment.
Figure 26:
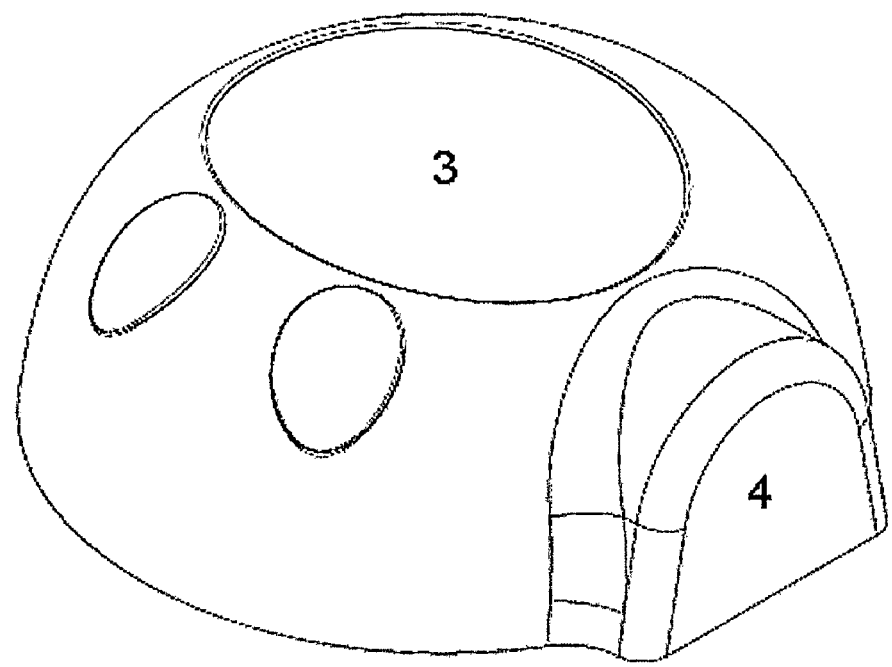
FIG. 26 shows a seventh embodiment having a base part equipped with a central combined connector and injection part.
Figure 26:
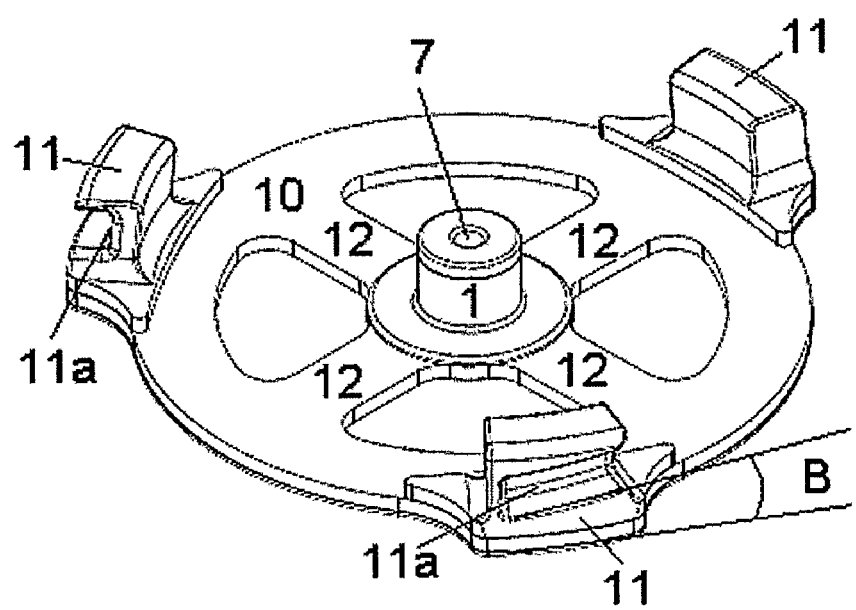
Figure 29:
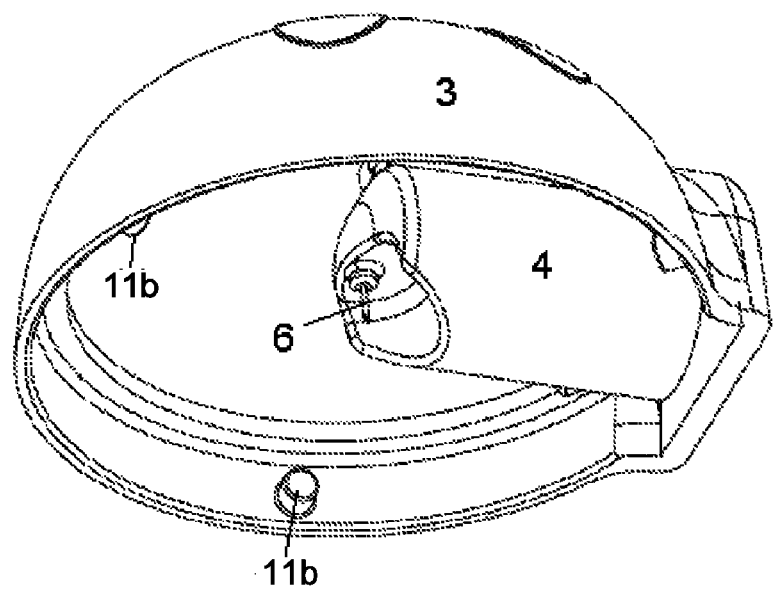
FIG. 29 shows a view from below of the delivery part of the seventh embodiment.

The injection part is a two-part unit comprising a first part 1*a* which is fastened unreleasably to the base plate 10 and a second part 1*b* comprising the cannula 9 which partly forms the fluid connection between the patient and the reservoir 4. A septum 7*a* is provided in the second part 1*b* as shown in FIGS. 20 and 24.

It is possible to position this embodiment on the skin of the patient applying at least two different methods. According to one method the base plate 10 comprising the first part 1*a* is first positioned on the skin of the patient and thereafter the cannula-holding second part 1*b* of the injection part 1 is injected e.g. with an especially adapted inserter, this method makes it possible for the user to exercise more care when positioning the base plate 10 which is normally equipped with an adhesive pad 35. According to a second method the base plate 10 comprising both the first part 1*a* and the cannula-holding second part 1*b* is injected all together with an inserter adapted to hold the entire device, this method comprises one less mounting step compared to the earlier described method.

In this embodiment the first part 1*a* is provided with inward projecting parts 1*c* and the second part 1*b* is provided with outward projecting, pivotably fastened hooks 1*d*. When the second part 1*b* is positioned in the first part 1*a*, the outward projecting hooks 1*d* are first pushed outward by the inward projecting parts 1*c* and after having passed the projecting parts 1*c*, the projecting hooks 1*d* return to their original position and locks the first part 1*a* inside the second part 1*a*.

The base plate 10 is provided with three upright positioned objects 11 for fastening of the delivery part 3, 4 to the base plate 10; the numbers of objects 11 are optional and the objects 11 can be either molded together with the base plate 10 or fastened to the base plate 10 after the base plate 10 has been formed e.g. by gluing or welding. The objects 11 are provided with sliding grooves 11*a* which sliding grooves 11*a* define the direction in which to move the delivery part 3, 4 when securing the delivery part 3, 4 to the base plate 10. The sliding grooves 11*a* correspond to protruding parts 11*b* on the delivery part 3, 4. In this embodiment the sliding grooves 11*a* are not parallel with the surface of the base plate 10 but differs in an angle B: 0°<B<45° where one side of the angle B is the distal surface of the base plate 10 and the other side of the angle B is the distal edge of the sliding grooves 11*a*. The angle B—together with the round shape of the delivery part 3, 4 and the central position of the connector 2—makes it possible to screw the delivery part 3, 4 on to the base plate 10.

The connector 2 is constructed of a molded body fastened unreleasably to the base plate 10 and provided with an interior compartment to which access is protected by a septum 7. The septum 7 is penetrated by the connector needle 6 when the delivery part 3, 4 is fastened to the base plate 10. From the lower part of the interior compartment and opening 5*a* allows fluid to enter into the flexible tube 5 and pass onto the patient through the cannula 9. The flexible tube 5 is connected to the first part 1*a* of the injection part and when the second part 1*b* of the injection part is positioned in the first part 1*a* a fluid path is created from the flexible tube 5 to the cannula 9.

The reservoir 4 of the shown embodiment will normally hold between 0.5-3 ml of fluid for transferal to the patient.

FIG. 26-29 shows an embodiment of the invention where the connector needle 6 is inserted directly into the injection part 1 i.e. there is no separate connection part. The injection part 1 is placed in a central position of the base plate 10 and therefore it is not possible for the user to observe the injection site.

In this embodiment the flexible portion 12 is also constructed from the base plate 10 and formed like four spokes in a wheel.

The injection part 1 is one unit comprising a molded body with an interior compartment. The interior compartment can be accessed through the protective seal 7 by the connector needle 6 when the delivery part 3 including the reservoir 4 is placed in correct position. From the interior compartment fluid can be channeled out through the cannula 9.

The base plate 10 is like the embodiment of FIG. 20-25 provided with three upright positioned objects 11 for fastening of the delivery part 3, 4 to the base plate 10; the numbers of objects 11 are optional.

In the embodiment of FIG. 26-29 the base plate 10 is placed on the skin of the patient simultaneously with injection of the cannula 9 of the injection part 1 and the cannula 9 is inserted in a 90° angle. In order to insert the device an inserter of the type shown in EP 1 429 826 can be used.

Figure 30:
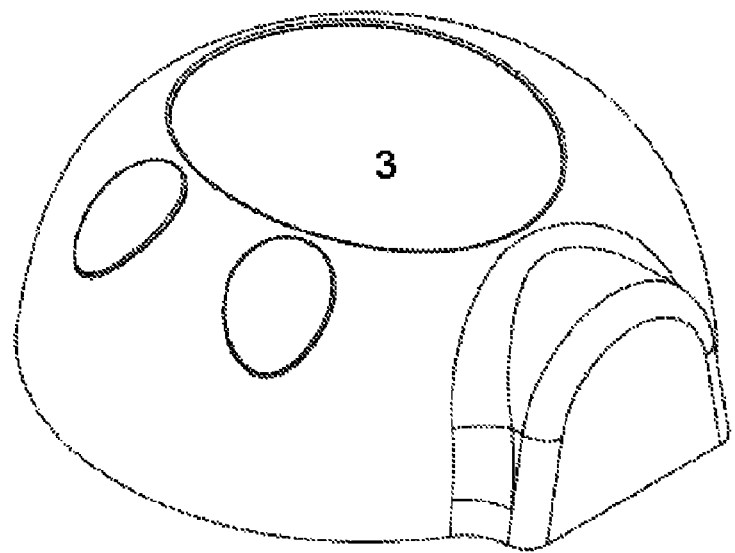
FIG. 30 shows an eighth embodiment having a base part equipped with a central combined connector and injection part where the combined part is divided into to units.
Figure 30:
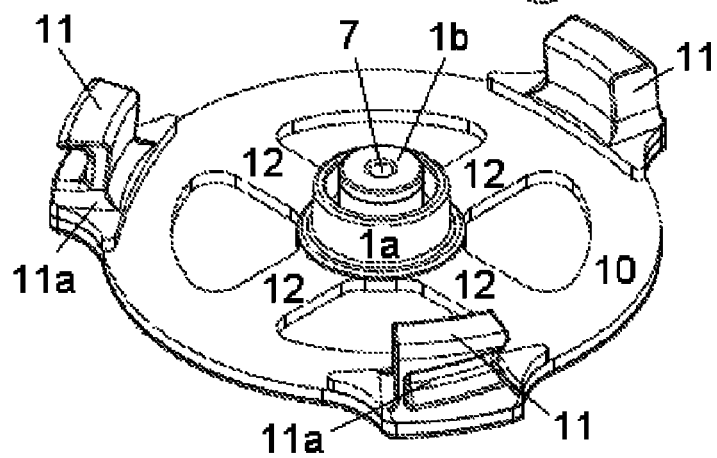
Figure 31:
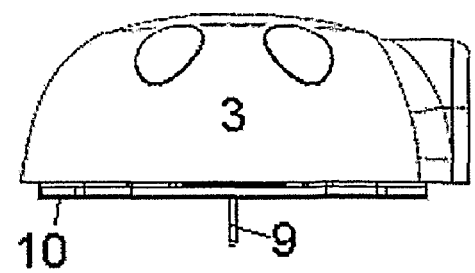
FIG. 31 shows the delivery device and the base part of the eighth embodiment in a joined state from above and from the side.
Figure 31:
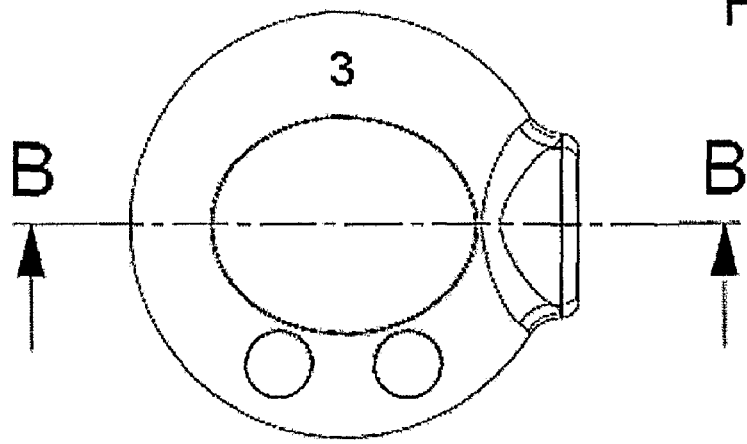
Figure 32:
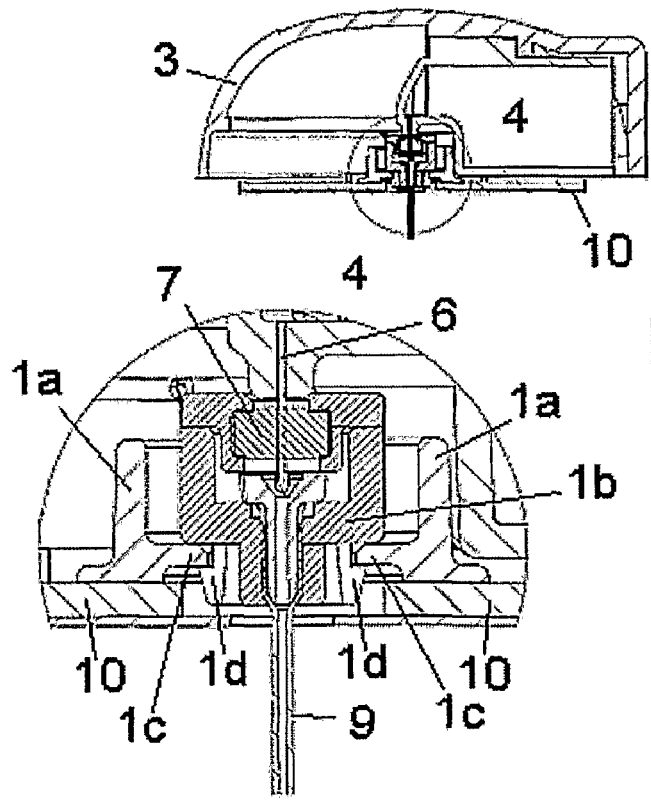
FIG. 32 shows a cut through view of the eighth embodiment in the joined state of FIG. 31 and an enlargement of the combined connector/injection part.
Figure 33:
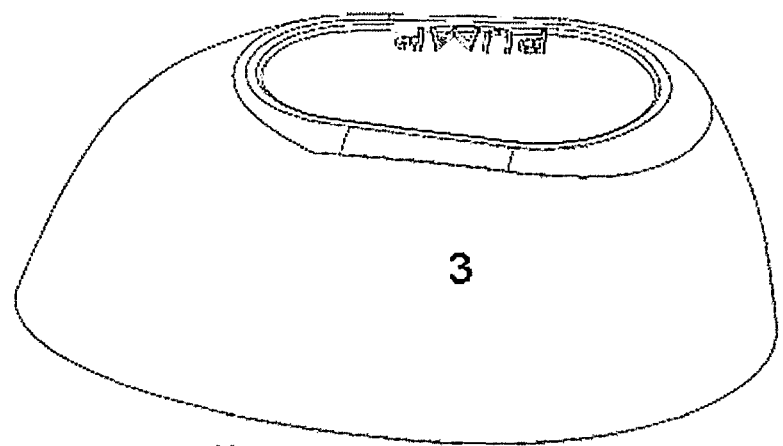
FIG. 33 shows a ninth embodiment having an oval base part equipped with a central connector and peripheral injection part.
Figure 34:
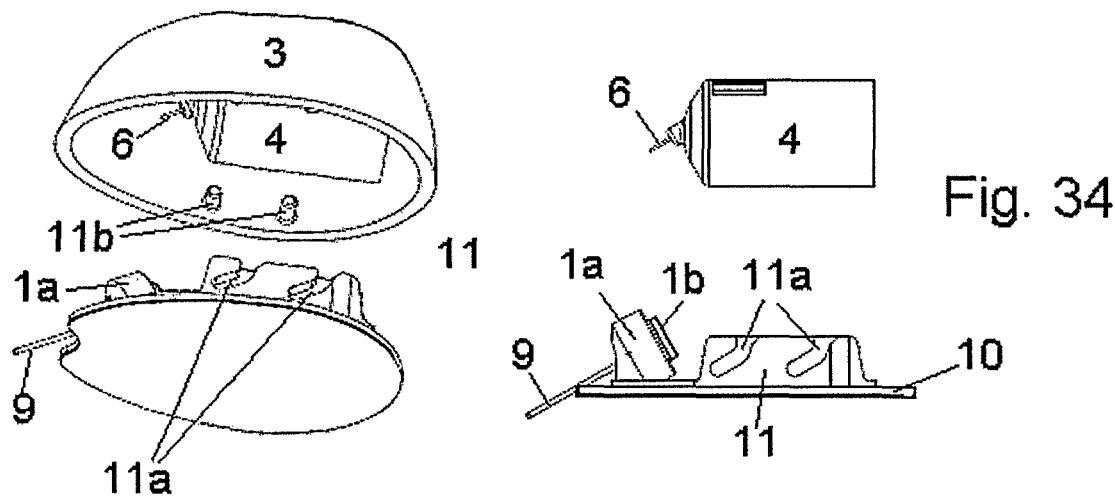
FIG. 34 shows the delivery device and the base part of the ninth embodiment in a separated state from below and the reservoir and the base part from the side.
Figure 35:
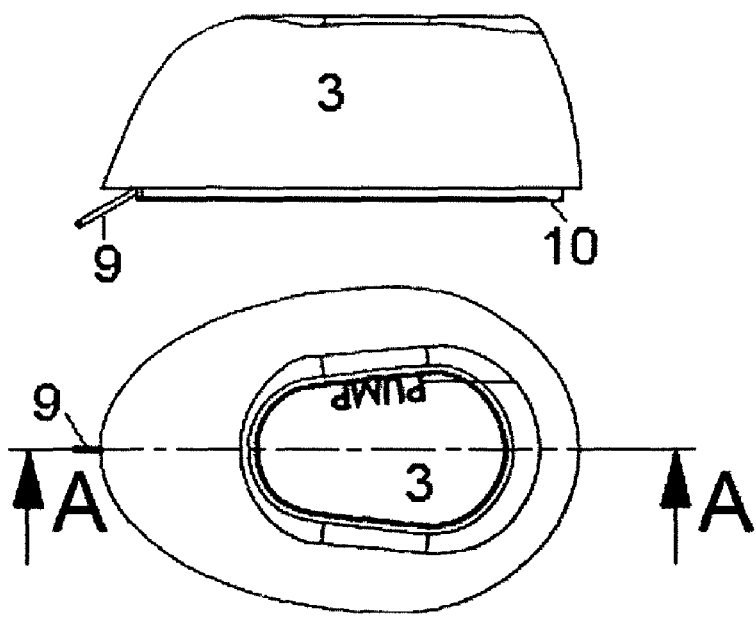
FIG. 35 shows the delivery device and the base part of the ninth embodiment in a joined state from the side and from above.
Figure 36:
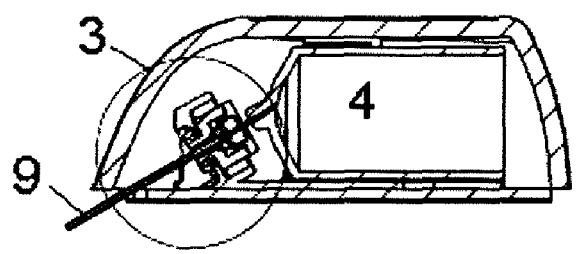
FIG. 36 shows a cut through view of the ninth embodiment in the joined state of FIG. 35 and an enlargement of the injection part.
Figure 36:
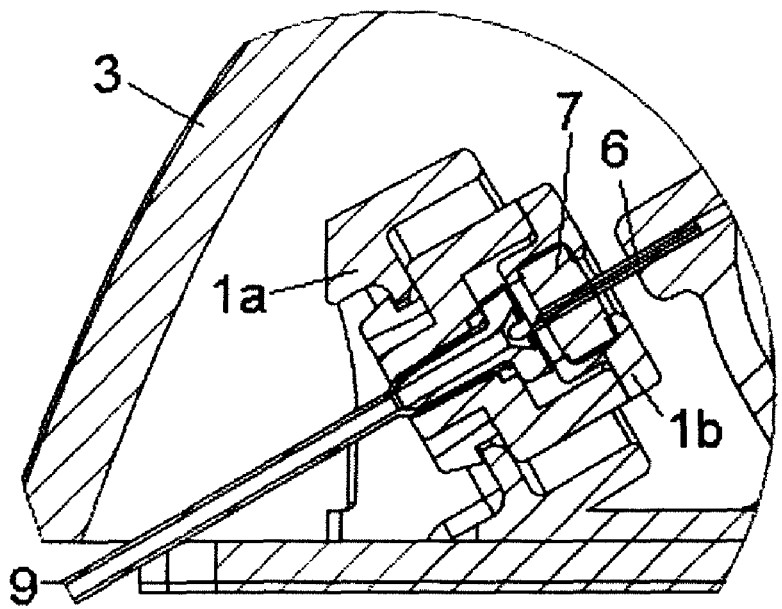

FIG. 30-32 shows an embodiment of the invention which as the embodiment of FIG. 26-29 is without a separate connector. The injection part is placed in a central position of the base plate 10 and therefore it is not possible for the user to observe the injection site.

In this embodiment the flexible portion 12 is also constructed from the base plate 10 and formed like four spokes in a wheel.

The injection part is a two-part unit comprising a first part 1*a* which is fastened unreleasably to the base plate 10 and a second part 1*b* comprising the cannula 9. According to this embodiment the base plate 10 is positioned on the skin of the patient first and then the cannula-holding part 1*b* of the injection part 1 is injected in the allocated position. Like the embodiment shown in FIG. 20-25 the first part 1*a* of this embodiment is provided with inward projecting parts 1*c* and the second part 1*b* is provided with outward projecting and pivotably fastened hooks 1*d* which corresponding parts can lock the second part 1*b* in the desired position.

FIG. 33-36 shows an embodiment of the invention where the injection part 1 is fastened to a peripheral part of the base plate 10 from which position it is possible to perform an angled injection and thereby making it possible for the user to observe the injection site. In this embodiment the injection part 1 is of the two-part type comprising a first part 1*a* which is fastened unreleasably to the base plate 10 and a second part 1*b* comprising the cannula 9. The first part 1*a* is provided with inward projecting parts 1*c* and the second part 1*b* is provided with outward projecting and pivotably fastened hooks 1*d*.

The flexible portion 12 of this embodiment is also constructed from the base plate 10 but here the flexible portion 12 is formed like a lattice. According to this embodiment it is also possible to vary the flexibility of the flexible portions 12 by varying the width of the portions 12, the thickness of the base plate material 10 or the number of portions i.e. bars 12.

The base plate 10 is provided with two upright positioned objects 11 for fastening of the delivery part 3, 4 to the base plate 10; the numbers of objects 11 are optional and the objects 11 can be either molded together with the base plate 10 or fastened to the base plate 10 after the base plate 10 has been formed e.g. by gluing or welding. The objects 11 are provided with sliding grooves 11a which sliding grooves 11a define the direction in which to move the delivery part 3, 4 when securing the delivery part 3, 4 to the base plate 10. In this embodiment each object 11 is provided with two sliding grooves 11a, and each sliding groove 11a is inclined in an angle B: 0°<B<90°. The sliding grooves 11a correspond to protruding parts 11b on the delivery part 3, 4. The interaction between the sliding grooves 11a of the base plate 10 and the protruding parts 11b of the delivery part 3 assures correct insertion of the connector needle 6 through the protective seal 7 of the injection part 1b as the delivery part 3 moves along a well defined path during fastening to the base plate 10.

Generally when the injection part 1 is constructed of a two-part unit 1a, 1b the method for fastening the device to the skin of the patient will comprise the following step:

If the base plate 10 is provided with an adhesive surface e.g. unreleasably combined to an adhesive pad, the adherent side of the base plate 10 is exposed e.g. by removing a release liner, the base plate 10 comprising a part of the injection part 1a is positioned on the skin of the patient, a second part of the injection part 1b is inserted into the position defined by the first part 1a, normally by use of an insertion device which could be a multi-use insertion device or a single-use insertion device, the delivery part 3 is positioned on top of the base plate 10.

The invention claimed is:

1. A device for delivering fluid comprising an injection part and a removably connected fluid delivery part, the fluid delivery part comprising:
   a reservoir, a pump, and a housing, the pump and the reservoir are covered with the housing, and
   the injection part comprising;
   a cannula part comprising a body with a through-going opening provided with a cannula;
   a base plate comprising a first part and a second part, the first part and the second part being configured to be fastened to the patient's skin, the cannula extending past a proximal side of the base plate, and
   an adhesive portion for fixation of the base plate to the skin of the patient;
   wherein the delivery part and the injection part are assembled through a connector comprising a fluid path configured to lead fluid from the reservoir to the through-going opening in the cannula part, wherein the delivery part is fastened to the first part of the base plate and the cannula part is fastened to the second part of the base plate; and
   wherein the delivery part and the injection part have at least two positions in relation to each other, a first position where the connector is disconnected from the delivery part and wherein an outlet from the reservoir is blocked with a first barrier which is not permeable for microorganisms and an inlet of the injection part is blocked with a second barrier which is reclosable and not permeable for microorganisms, and a second position wherein an open fluid connection is formed between the reservoir and the through-going opening in the cannula part.

2. A device according to claim 1, wherein the base plate comprises a fastener for connecting and disconnecting the delivery part, the fastener extending from a distal side of the base plate.

3. A device according to claim 1, wherein the fluid path is blocked with the second barrier comprising a membrane that can be penetrated by a needlelike object.

4. A device according to claim 1, wherein one or both of the barriers comprise a material that is penetratable by a needlelike object and reclosable on retraction of the needlelike object.

5. A device according to claim 4, characterized in that the needlelike object is blunt.

6. A device according to claim 4, characterized in that the needlelike object is sharp-pointed.

7. A device according to claim 1, wherein one or both of the barriers comprise a hard surface.

8. A device according to claim 1, wherein the delivery part is releasably fastened to the base plate.

9. A device according to claim 1, wherein the connector is fastened to the first part of the base plate.

10. A device according to claim 1, wherein the cannula has a proximal end protruding from a proximal side of the body of the injection part.

11. A device according to claim 1, wherein the device is fastened to the patient's skin by applying a mounting pad adhered to the proximal side of the base plate.

12. A device for delivering fluid comprising an injection part and a removably connected fluid delivery part, the fluid delivery part comprising:
   a reservoir, a pump, and a housing, the pump and the reservoir are covered with the housing, and
   the injection part comprising;
   a cannula part comprising a body with a through-going opening provided with a cannula;
   a base plate comprising a first part and a second part, the first part and the second part being configured to be fastened to the patient's skin, the cannula extending past a proximal side of the base plate, and
   an adhesive portion for fixation of the base plate to the skin of the patient;
   wherein the delivery part and the injection part are assembled through a connector comprising a fluid path configured to lead fluid from the reservoir to the through-going opening in the cannula part, wherein the delivery part is fastened to the first part of the base plate and the cannula part is fastened to the second part of the base plate; and
   wherein the delivery part and the injection part have at least two positions in relation to each other, a first position where the connector is disconnected from the delivery part and wherein an outlet from the reservoir is blocked with a first barrier which is not permeable for microorganisms and an inlet of the injection part is blocked with a second barrier which is reclosable and not permeable for microorganisms, and a second position wherein an open fluid connection is formed between the reservoir and the through-going opening in the cannula part; and
   wherein the first part and the second part of the base plate are connected to each other by at least one flexible area.

* * * * *